United States Patent [19]
Yoon

[11] Patent Number: 5,833,695
[45] Date of Patent: Nov. 10, 1998

[54] SURGICAL STAPLING SYSTEM AND METHOD OF APPLYING STAPLES FROM MULTIPLE STAPLE CARTRIDGES

[76] Inventor: InBae Yoon, 2101 Highland Ridge Dr., Phoenix, Md. 21131

[21] Appl. No.: 375,120

[22] Filed: Jan. 19, 1995

Related U.S. Application Data

[63] Continuation-in-part of Ser. No. 274,402, Jul. 13, 1994.

[51] Int. Cl.[6] .................................................. A61B 17/04
[52] U.S. Cl. ...................... 606/139; 606/219; 227/176.1; 227/177.1; 227/179.1
[58] Field of Search .................................. 227/175–180; 606/139, 143

[56] References Cited

U.S. PATENT DOCUMENTS

| | | |
|---|---|---|
| 2,638,901 | 5/1953 | Sugarbaker . |
| 3,080,564 | 3/1963 | Strekopitov et al. . |
| 3,166,072 | 1/1965 | Sullivan, Jr. . |
| 3,490,675 | 1/1970 | Green et al. . |
| 3,589,589 | 6/1971 | Akopov . |
| 3,882,854 | 5/1975 | Hulka et al. . |
| 4,064,881 | 12/1977 | Meredith . |
| 4,198,982 | 4/1980 | Fortner et al. . |
| 4,354,628 | 10/1982 | Green . |
| 4,523,592 | 6/1985 | Daniel . |
| 4,548,201 | 10/1985 | Yoon . |
| 4,548,202 | 10/1985 | Duncan . |
| 4,624,257 | 11/1986 | Berggren et al. . |
| 4,633,874 | 1/1987 | Chow et al. . |
| 4,749,114 | 6/1988 | Green . |
| 4,794,927 | 1/1989 | Yoon . |
| 4,821,719 | 4/1989 | Fogarty . |
| 4,930,674 | 6/1990 | Barak . |
| 5,015,249 | 5/1991 | Nakao et al. . |
| 5,040,715 | 8/1991 | Green et al. . |
| 5,049,153 | 9/1991 | Nakao et al. . |
| 5,074,454 | 12/1991 | Peters . |
| 5,100,418 | 3/1992 | Yoon et al. . |
| 5,156,609 | 10/1992 | Nakao et al. . |
| 5,156,614 | 10/1992 | Green et al. . |
| 5,158,567 | 10/1992 | Green . |
| 5,171,250 | 12/1992 | Yoon . |
| 5,171,253 | 12/1992 | Klieman . |
| 5,209,756 | 5/1993 | Seedhom et al. . |
| 5,222,961 | 6/1993 | Nakao et al. . |
| 5,242,457 | 9/1993 | Akopov et al. . |
| 5,258,008 | 11/1993 | Wilk . |
| 5,263,629 | 11/1993 | Trumbull et al. ........................ 227/175 |
| 5,330,486 | 7/1994 | Wilk . |
| 5,366,458 | 11/1994 | Korthoff et al. . |
| 5,366,459 | 11/1994 | Yoon . |
| 5,376,095 | 12/1994 | Ortiz . |
| 5,395,034 | 3/1995 | Allen et al. .............................. 227/178 |
| 5,417,361 | 5/1995 | Williamson, IV ...................... 227/176 |

*Primary Examiner*—Gary Jackson

[57] ABSTRACT

A surgical stapling system includes a staple cartridge having a pair of generally coextensive cartridge bodies adapted to fit within opposed jaws of a stapling instrument and one or more staples carried by a first of the cartridge bodies in opposed relation to apertures or anvils formed in a second of the cartridge bodies. The cartridge bodies are preferably and advantageously made of bioabsorbable materials so that they can be left in place within the body and so that another staple cartridge can be advanced between the opposed jaws of the stapling instrument without the need of having to withdraw the stapling instrument from the body.

48 Claims, 17 Drawing Sheets

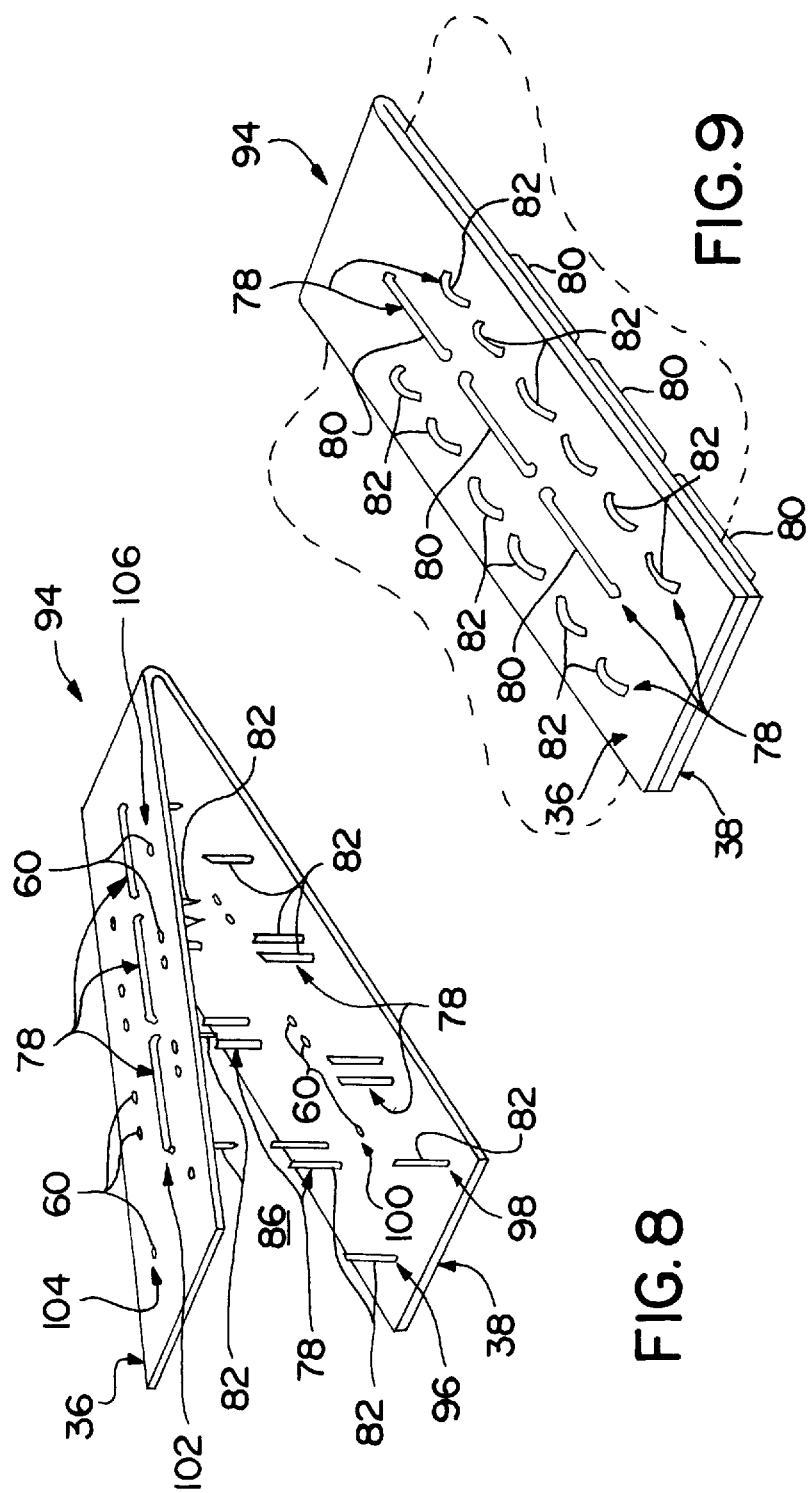

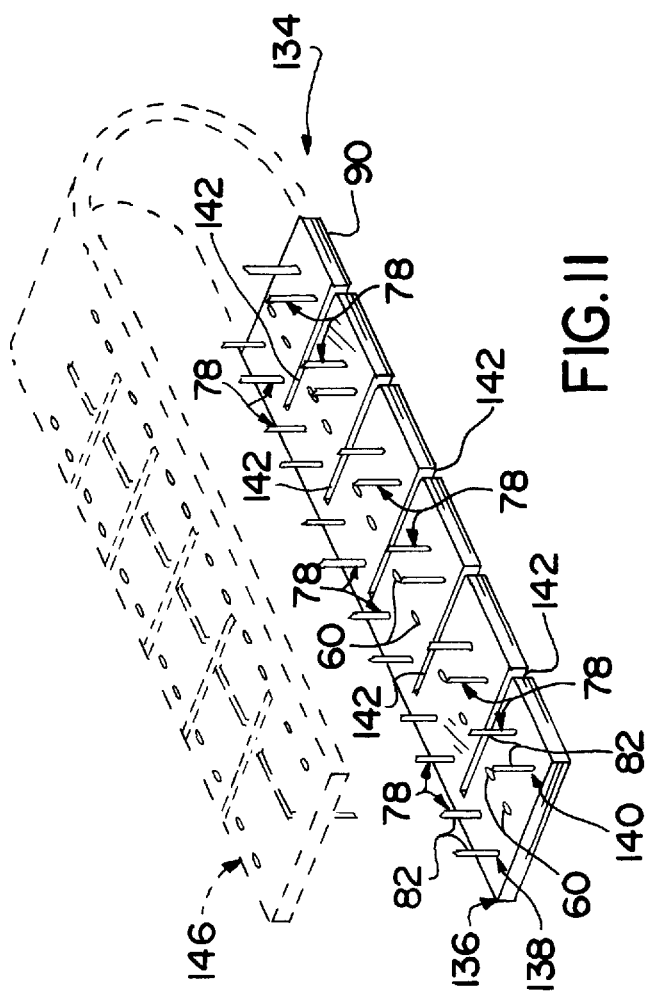
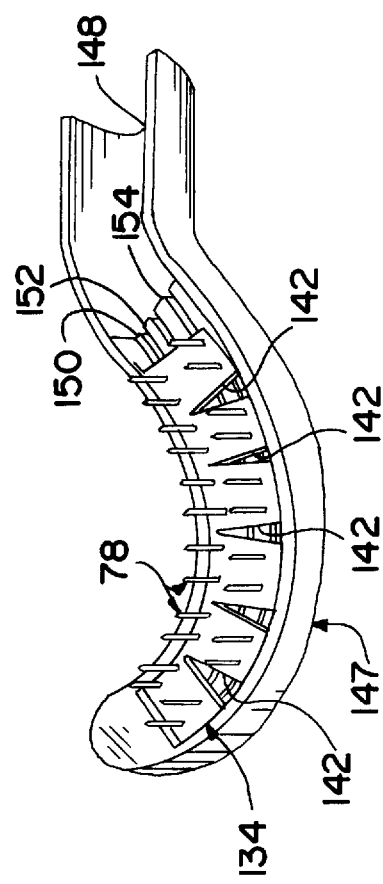

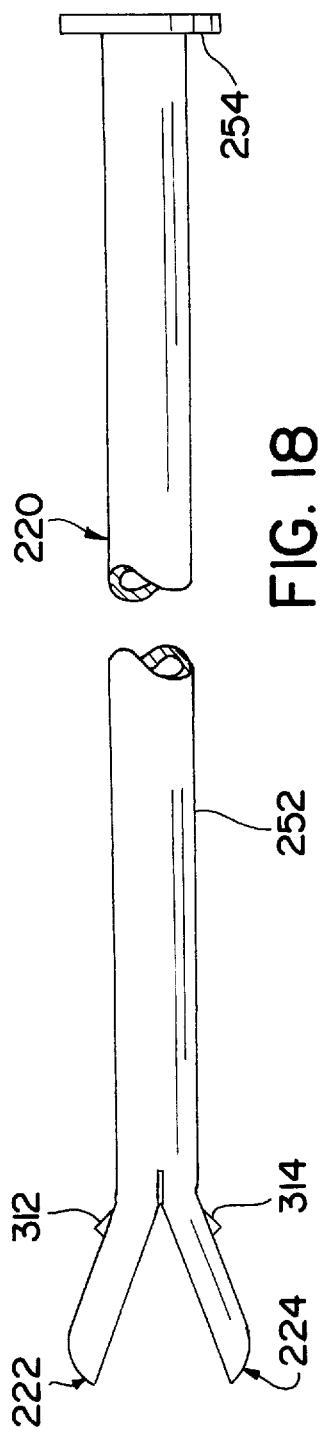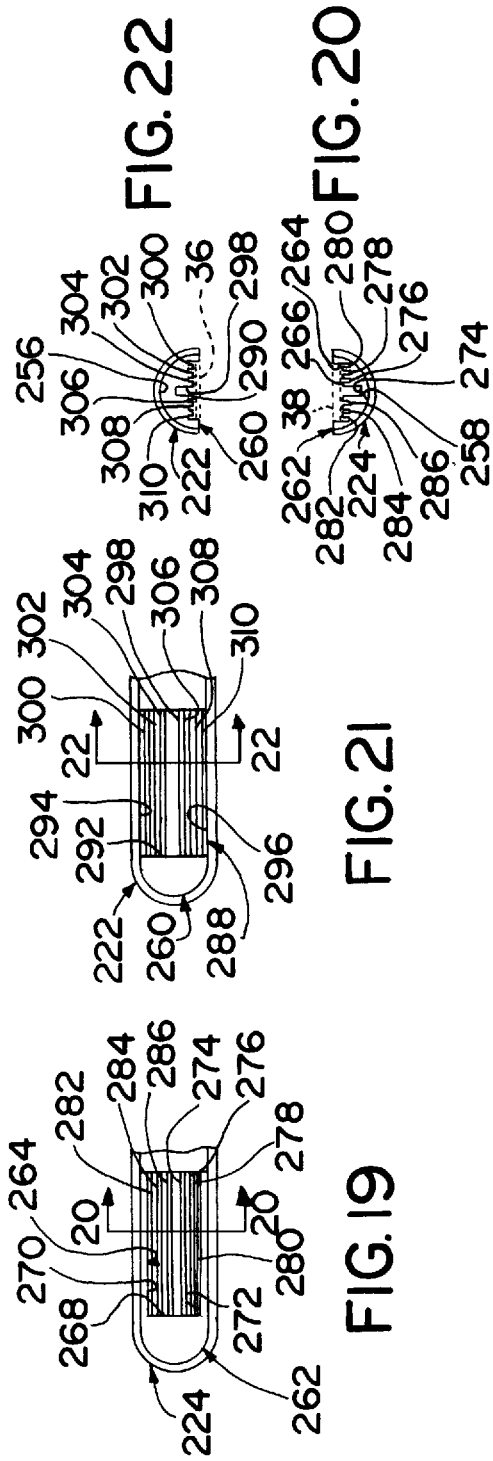

SURGICAL STAPLING SYSTEM AND METHOD OF APPLYING STAPLES FROM MULTIPLE STAPLE CARTRIDGES

CROSS REFERENCE TO RELATED APPLICATIONS

This application is a continuation-in-part of applicant's patent application Ser. No. 08/274,402, filed Jul. 13, 1994, now abandoned, the disclosure of which is incorporated herein by reference.

BACKGROUND OF THE INVENTION

1. Field of the Invention

The present invention relates generally to medical procedures and instruments and, more particularly, to surgical staple cartridges, stapling instruments for applying staples carried by such surgical staple cartridges, and methods of applying staples to bodily tissue from a number of surgical staple cartridges without the need of having to withdraw stapling instruments from the surgical field.

2. Discussion of the Prior Art

Suturing tissue and organs is a painstaking and time-consuming part of most surgical procedures. A high degree of skill is needed and the time and care required increases both the cost of surgery, the potential for excessive blood loss and the risk to the patient accompanying prolonged anesthetization. The advent of surgical staplers has facilitated the suturing process in many procedures, allowing uniform and consistent tissue-fastening to be accomplished with the squeeze of a handle or the advancement of a pusher bar after positioning the stapling instrument.

Surgical staplers have evolved into two common forms. In one form, an instrument body has a U-shaped distal portion with a proximal movable jaw generally perpendicular to the instrument body and a distal anvil jaw fixedly or pivotally mounted to a lower portion of the movable jaw. Spaced parallel rows of distally directed staples are inserted into the movable jaw, tissue to be fastened is positioned between the jaws and the jaws are compressed against the tissue to a preset separation gap. A distal force is applied from the handle to drive movable pushers or hammers in the movable jaw distally forcing the staples out of the cartridge, through the tissue and into the anvil jaw where the staple legs are crimped to fasten the tissue. U.S. Pat. No. 3,080,564 to Strekopitor et al is exemplary of such staplers. Later developments resulted in the adaptation of the instrument to use preloaded replaceable cartridges carrying a plurality of staples instead of having to tediously reload the movable jaw with individual staples between uses. U.S. Pat. No. 3,589,589 to Akopov exemplifies such instruments. Fully disposable versions of this basic stapler form have been produced as well, primarily to avoid the work and cost associated with proper disassembly, sterilization and reassembly required for reuse.

The second common form of stapling instrument typically has a pair of elongate blunt-nosed jaws extending distally from the handle, one jaw holding a cartridge in which two or more rows of staples are held with the tissue penetrating staple legs aligned perpendicular to the opposite jaw face and the opposed jaw supporting rows of anvils with curved indentations aligned with the staple legs in the cartridge. These indentations bend and clinch the staple legs as the staples are driven into them. U.S. Pat. No. 3,490,675 to Green is exemplary of such stapling instruments. In use, the jaws of these instruments are positioned on either side of the tissue to be joined and then closed to a preset separation gap with the tissue held therebetween. A pusher bar, slidably mounted along the instrument body between the handle and the staple cartridge, is advanced distally into the staple carrying cartridge to individually cam driver bars, or hammers, which sequentially force the staples from the cartridge, into and through the tissue to be joined and into the anvils. Usually such instruments also incorporate a knife blade that is driven in tandem with the clinching of the staple legs to produce a clear cut in the tissue between linear rows of staples. After the staples have been forced from the cartridge, the stapling instrument is typically removed from the surgical field so that the spent cartridge can be ejected or retrieved from between the jaws.

Other instruments apply two-piece surgical fasteners. These fasteners are typically made from biologically absorbable or non-absorbable polymeric materials which cannot maintain a bent or crimped configuration after being deformed. Hence, in addition to a tissue penetrating member having one or more prongs which are driven through one side of the tissue to be joined, such fasteners also require a retaining member which is positioned on the other side of the tissue to receive the prongs of the tissue penetrating member in an interlocking fashion. One such fastener structure and apparatus for applying it are disclosed in U.S. Pat. No. 5,156,614 to Green.

Unlike staples, two-piece polymeric fasteners require the fabrication of a plurality of differently sized components. Also, when utilizing two-piece fasteners, alignment between the tissue penetrating member and receiving member is critical. A concern with bioabsorbable two-piece fasteners, in particular, is whether the will have sufficient strength to hold the tissue together for a sufficient period of time to allow the tissue to heal prior to being absorbed.

Recently, the adaptation of a stapling instrument to laparoscopic and endoscopic procedures has appeared, as exemplified by U.S. Pat. No. 5,050,715 to Arein et al. This apparatus includes an elongate tube-like body connecting a handle, positioned external to the surgical site, and two opposed jaws, aligned generally coaxially with the body and positionable at the surgical site. A cartridge of staples is carried in one of the jaws and the opposed jaw functions as an anvil. Tissue is clamped between the jaws, then staple driving bars are driven through the cartridge by a series of cam bars to sequentially force the staples through the tissue and into the anvil for clinching.

While prior art stapling instruments are widely used, they suffer from many disadvantages when used in procedures requiring lines of staples to be applied at more than one location. One of the disadvantages of prior art stapling instruments is that they must be removed from the surgical field to be reloaded after applying staples from a single cartridge. Consequently, if lines of staples are to be applied at more than one location, the spent cartridge must be removed from the jaws of the stapling instrument and another cartridge inserted or a second stapling instrument substituted for the first. In endoscopic procedures, such as laparoscopy, stapling instruments are passed through portals formed in the walls of anatomical cavities. Since it is generally desirable to minimize the number and size of incisions created for performing a particular endoscopic procedure, concurrent placement of stapling instruments through multiple portals created in the wall of a cavity is unacceptable. Moreover, substitution of multiple stapling instruments through a single incision or frequent withdrawal of a single stapling instrument for reloading can be time consuming, increasing the period of anesthetization for the patient and increasing the risk of bodily fluids obscuring the field of view.

SUMMARY OF THE INVENTION

Accordingly, it is a primary object of the present invention to overcome the above mentioned disadvantages of the prior art by providing a surgical stapling instrument capable of applying staples from multiple staple cartridges in succession without the need of having to be withdrawn from the surgical field.

Another object of the present invention is to eliminate the need for retrieving spent staple cartridges from the surgical field by forming the staple cartridges of bioabsorbable materials.

It is a further object of the present invention to apply a more uniform pressure across stapled tissue by using the staple cartridge as a pressure plate disposed between bent tissue penetrating legs of a staple and the stapled tissue.

Yet another object of the present invention is to reduce the need for frequent substitution of instruments during an endoscopic procedure by carrying out multiple functions with a single endoscopic instrument having a forceps unit that remains within an anatomical cavity and interchangeable operating units, one of which carries a plurality of staple cartridges and means for advancing the staple cartridges between jaws of the forceps unit.

Some of the advantages of the present invention over the prior art are that the surgical stapling instrument of the present invention eliminates the need for frequent withdrawal of stapling instruments from the surgical field to replace spent cartridges, that contact with a distal end of the surgical stapling instrument can be minimized during loading and reloading procedures to reduce the risk of exposing medical personnel to body fluids, that the time required for reloading stapling instruments can be reduced, that conventional handle structures can be used to provide users with a familiar feel and to decrease the time needed for adapting to the instrument, that the instrument can be fabricated at low cost using simple mechanisms without complicated linkages, and that the instrument can be sterilized for reuse or disposable for single patient use as desired.

The present invention is generally characterized in a staple cartridge including a pair of generally coextensive cartridge bodies adapted to fit within opposed jaws of a forceps and a plurality of staples carried by a first of the cartridge bodies and having ductile tissue penetrating legs, wherein a second of the cartridge bodies defines a plurality of spaces in opposed relation to the tissue penetrating legs of the staples. In one embodiment, the spaces are defined by grooves or cavities serving as anvils for bending the tissue penetrating legs of the staples as they are received. Alternatively, the spaces can be defined by apertures extending through the cartridge body to allow passage of the tissue penetrating legs of the staples. The cartridge bodies are preferably and advantageously made of bioabsorbable materials so that they can be left in place within the body.

Another aspect of the present invention is generally characterized in a surgical stapler including a housing, a forceps having an elongate tubular body with a proximal end mounted by the housing and a distal end forming opposed jaws, means for storing a plurality of staple cartridges within the elongate body of the forceps, means for advancing the staple cartridges distally for positioning between the opposed jaws of the forceps and means for at least partly closing the jaws to drive the tissue penetrating legs of the staples from a cartridge held between the jaws.

A further aspect of the present invention is generally characterized in a method of stapling anatomical tissue including the steps of positioning the anatomical tissue between generally opposed cartridge bodies of a staple cartridge, compressing the staple cartridge around the anatomical tissue, penetrating through the anatomical tissue with ductile tissue penetrating legs of one or more staples carried by one of the cartridge bodies, receiving the tissue penetrating legs of the staples in spaces defined in the opposed cartridge body and bending the tissue penetrating legs to form loops constricting the anatomical tissue.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 8 is a perspective view of a modified staple cartridge according to the present invention.

FIG. 9 is a perspective view of the modified staple cartridge of FIG. 8 applied to anatomical tissue.

FIG. 11 is a perspective view of yet another modification of the staple cartridge of the present invention.

FIG. 12 is a perspective view illustrating use of the staple cartridge of FIG. 11.

FIG. 18 is a broken side view of an intermediate member of the surgical stapling instrument of FIG. 16.

FIG. 19 is a fragmentary top view of a lower jaw formed at a distal end of the intermediate member shown at FIG. 18.

FIG. 20 is a cross-sectional view taken through line 20—20 in FIG. 19.

FIG. 21 is a fragmentary bottom view of an upper jaw formed at a distal end of the intermediate member shown in FIG. 18.

FIG. 22 is a cross-sectional view taken through line 22—22 in FIG. 21.

DETAILED DESCRIPTION OF THE PREFERRED EMBODIMENTS

Figure 1:
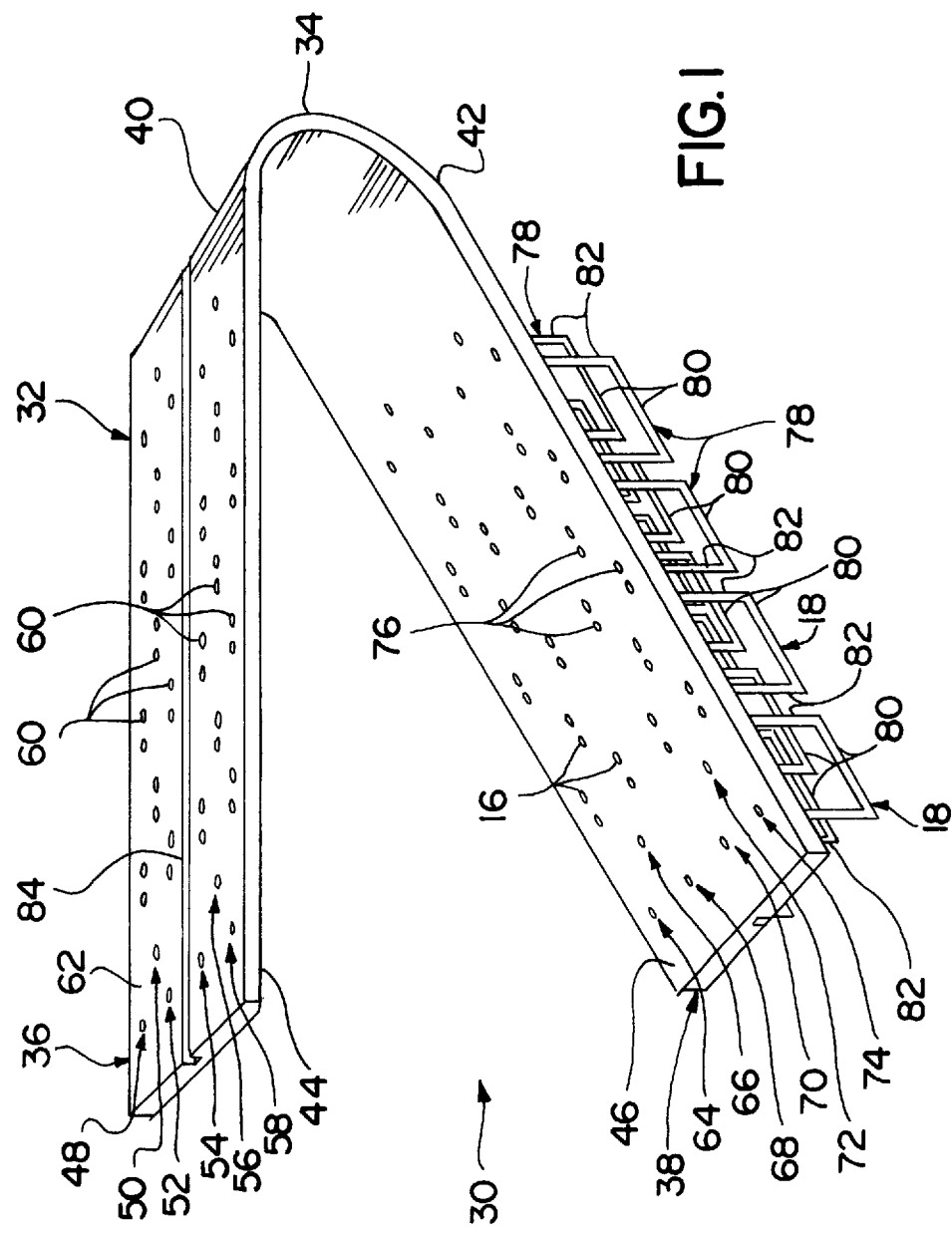
FIG. 1 is a perspective view of a staple cartridge according to the present invention.

A surgical stapling cartridge 30 according to the present invention is illustrated in FIG. 1. The surgical staple cartridge 30 includes a deformable strip 32 of medically-acceptable bioabsorbable or non-bioabsorbable material configured to form a rounded hinge or base 34 and a pair of generally opposed coextensive cartridge bodies 36 and 38 diverging from opposite ends 40 and 42 of the hinge.

Cartridge bodies 36 and 38 are generally rectangular in cross-section and define opposed tissue-engaging inner faces 44 and 46. Six parallel rows 48, 50, 52, 54, 56 and 58 of spaced openings or apertures 60 are formed through the upper cartridge body 36 and made to extend from the inner face 44 of the cartridge body to an outer face 62. Rows 48, 50, 52, 54, 56 and 58 each include eight apertures 60 arranged linearly along respective longitudinal axes of the cartridge body 36. Outermost and innermost pairs of rows 48, 58, 52 and 54 are coextensive and longitudinally aligned. Intermediate rows 50 and 56 are longitudinally offset from the outermost and innermost pairs of rows so that the apertures in rows 50 and 56 are aligned longitudinally with interstices between the apertures of rows 48, 58, 52 and 54. Six rows 64, 66, 68, 70, 72 and 74 of openings or apertures 76 are also formed in the lower cartridge body 38 in opposed relation to apertures 60. Twenty four staples 78, each having a cross member 80 and a pair of tissue penetrating legs 82 extending perpendicularly from opposed ends of the cross member, are arranged in six rows beneath the lower cartridge body 38 with the tissue penetrating ends of the legs 82 held within openings 76. A slot or groove 84 extends along a central longitudinal axis of the strip 32 dividing the surgical staple cartridge 30 into a pair of laterally symmetric halves joined by a thin web at the bottom of the groove. Each half of the surgical staple cartridge 30 contains three rows of staples.

Staples 78 can be made of any medically-acceptable material that is ductile, malleable or plastically deformable (that is, any material that when bent remains in the bent condition) including stainless steel, titanium, tantalum and other non-bioabsorbable and bioabsorbable materials. The legs 82 are held within openings 76 by friction fit, adhesive bonding or by any other suitable method of attachment.

Operation of the surgical staple cartridge 30 for applying surgical staples to anatomical tissue will now be described with reference to FIGS. 2–5 wherein, for purposes of clarity, only a single row of staples is illustrated.

Figure 2:
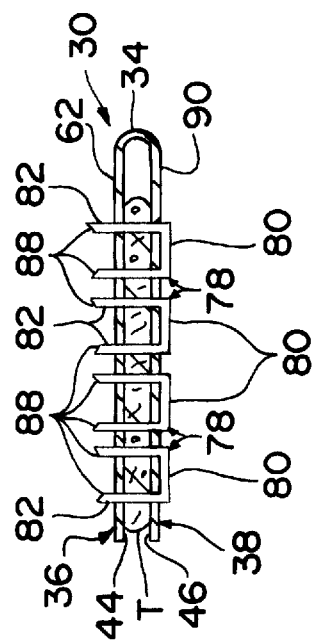
FIGS. 2–5 are side views, partly in section, illustrating use of the staple cartridge of FIG. 1.
Figure 3:
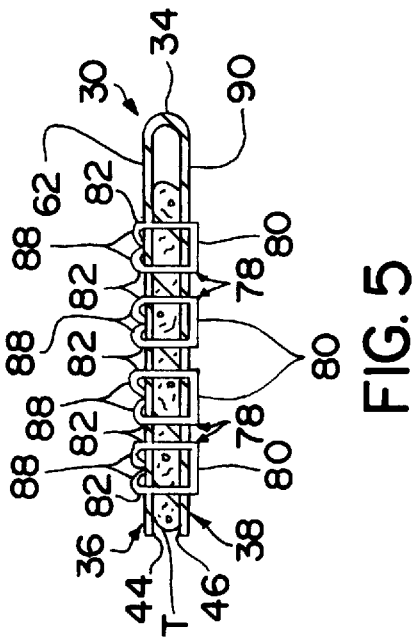
Figure 4:
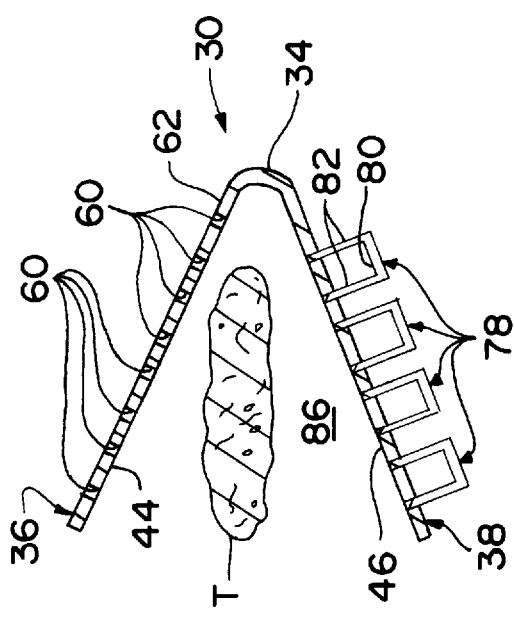
Figure 5:
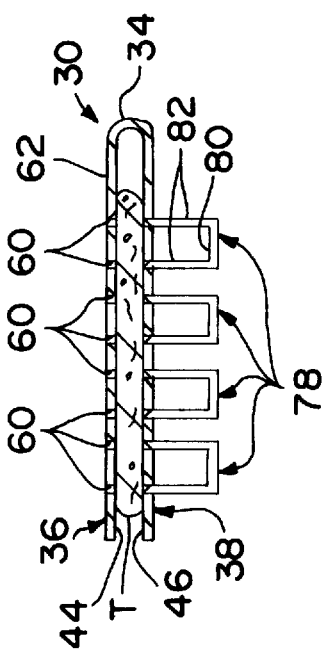
Figure 6:
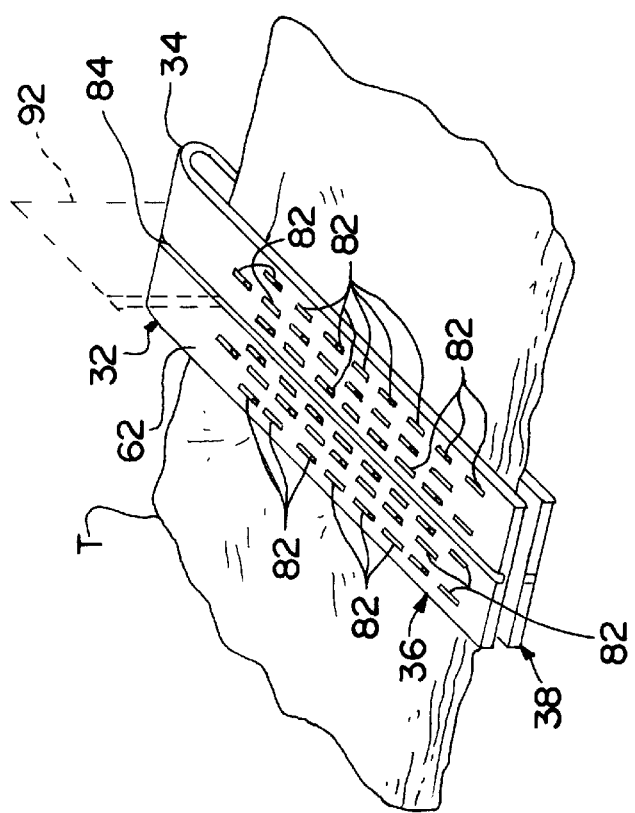
FIG. 6 is a perspective view of the staple cartridge of FIG. 1 applied to anatomical tissue.
Figure 16:
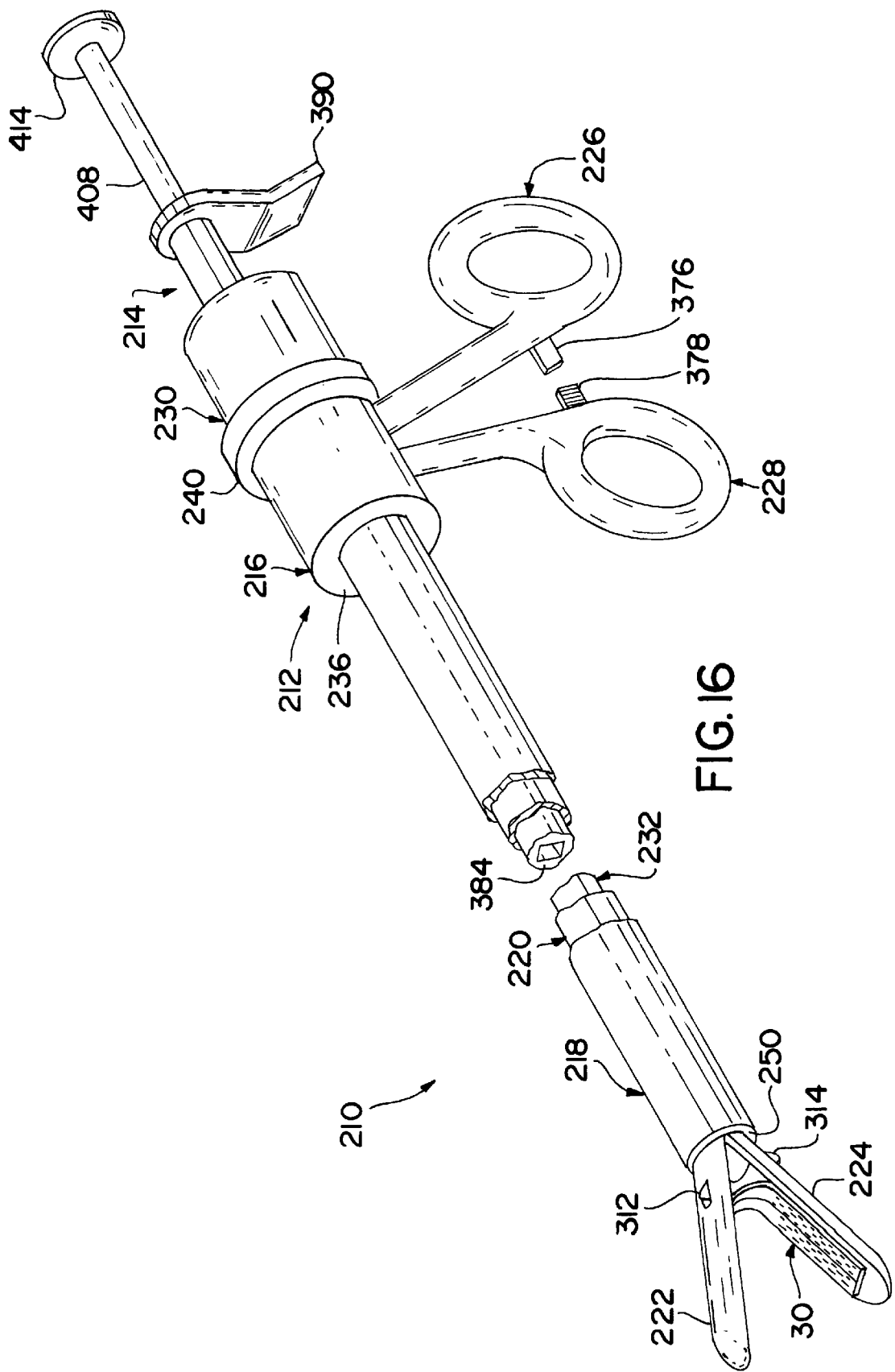
FIG. 16 is a perspective view of a surgical stapling instrument according to the present invention.

In use, cartridge bodies 36 and 38 of the surgical staple cartridge 30 are held between jaws of a stapling instrument, an example of which is shown in FIG. 16 and described in more detail below, and are positioned on opposite sides of anatomical tissue to be stapled. The cartridge bodies 36 and 38 are normally biased apart so that, when jaws of the stapling instrument are open, the surgical staple cartridge 30 will appear as illustrated in FIG. 2 with cartridge bodies 36 and 38 spread apart to define a space 86 for receiving the anatomical tissue T. The cartridge bodies 36 and 38 are moved toward one another by closing the jaws of the stapling instrument around the surgical staple cartridge 30. The jaws are configured to engage the outer face 62 of the upper cartridge body 36 and the staple cross members 80 so that the cartridge bodies are made to rotate toward one another about hinge 34 when the jaws are closed. Since there is no contact with the anatomical tissue T initially there is no counterforce exerted on the inner faces 44 and 46 of the cartridge bodies and thus the staple legs 82 are not forced through the openings in the lower cartridge body 38. When contact is made with the anatomical tissue T as shown in FIG. 3, the tissue exerts a counterforce against the inner faces 44 and 46 of the cartridge bodies resisting further movement of the cartridge bodies. As a result, continued compression of the surgical staple cartridge 30 drives the staple legs 82 through the openings in the lower cartridge body 38 and into the anatomical tissue T. The tissue penetrating tips 88 of the staple legs 82 are received by apertures 60 in the upper cartridge body 36 and protrude from the apertures 60 when the staple cross members 80 abut an outer face 90 of the lower cartridge body 38, as shown in FIG. 4. The protruding tips 88 of the staple legs bear against the upper jaw of the stapling instrument or an anvil structure supported by the upper jaw of the stapling instrument and are bent or crimped as shown in FIGS. 5 and 6 to prevent separation of the cartridge bodies 36 and 38 from the anatomical tissue T held therebetween.

Figure 7:
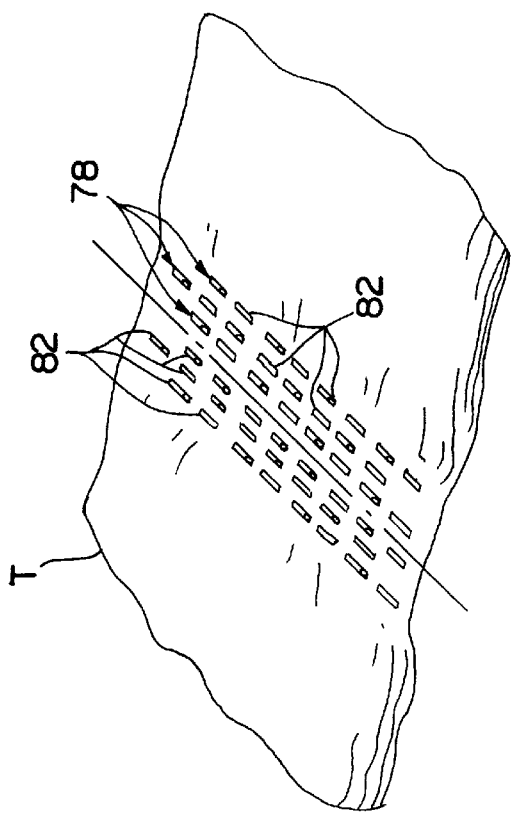
FIG. 7 is a perspective view of the stapled anatomical tissue shown in FIG. 6 after portions of the staple cartridge have been absorbed.

Since the cartridge bodies 36 and 38 are stapled together with the anatomical tissue T, the surgical staple cartridge 30 will remain on the stapled tissue when the jaws of the stapling instrument are opened, obviating the need for manually retrieving the staple cartridge after the staples have been applied. Moreover, by holding the cartridge bodies in compression against the anatomical tissue T, the cartridge bodies serve as pressure plates evenly distributing the compressive loads applied by the staples and creating a more uniform seal across the anatomical tissue. As illustrated in FIG. 6, the anatomical tissue T can be transected between rows of staples by advancing a blade, shown in phantom at 92, along the groove 84 formed along the central longitudinal axis of the strip 32 defining the upper and lower cartridge bodies 36 and 38. If made of bioabsorbable materials, the cartridge bodies 36 and 38 will be absorbed over time, as shown in FIG. 7, leaving only the staples.

A modified surgical staple cartridge 94 according to the present invention is illustrated in FIG. 8. The modified surgical staple cartridge 94 is similar to the surgical staple cartridge 30 depicted in FIG. 1 with the primary difference being that staples are applied from both cartridge bodies to provide visual confirmation from either side of the surgical staple cartridge that the tissue has been properly fastened. Lower cartridge body 38 carries two rows 96 and 98 of staples 78 arranged end-to-end in groups of three with their legs 82 protruding from openings in the cartridge body 38 and extending into the space 86 between the cartridge bodies. A row 100 of spaced apertures 60 is formed intermediate staple rows 96 and 98 in the lower cartridge body 38 and is aligned longitudinally with interstices between openings 76 in the lower cartridge body. A row 102 of three staples 78 is carried by upper cartridge body 36 with legs 82 of the staples protruding from openings in the upper cartridge body opposite apertures 60 in the lower cartridge body. Two rows 104 and 106 of apertures 60 are formed on either side of staple row 102 in upper cartridge body 36 in opposition to staple legs 82 protruding from lower cartridge body 38.

It will be appreciated that since legs 82 of the staples 78 extend into the tissue receiving space 86 between the cartridge bodies, the sharp tissue penetrating tips 88 of the legs will be exposed when the cartridge bodies are biased apart as shown in FIG. 8. Thus, when positioning the surgical staple cartridge 94 around anatomical tissue, the tissue will fit in the space between the tissue penetrating tips 88 of opposed staples carried by respective cartridge bodies. Once positioned around anatomical tissue, slight compression of the surgical staple cartridge 94 will drive the staple legs into the anatomical tissue immobilizing the tissue while the stapling procedure is performed. When fully compressed, upper and lower cartridge bodies 36 and 38 will both be held by a plurality of crimped staple legs 82 and cross members 80, as shown in FIG. 9, providing visual confirmation from either side of the surgical staple cartridge that the stapling procedure has been successfully accomplished.

Figure 10:
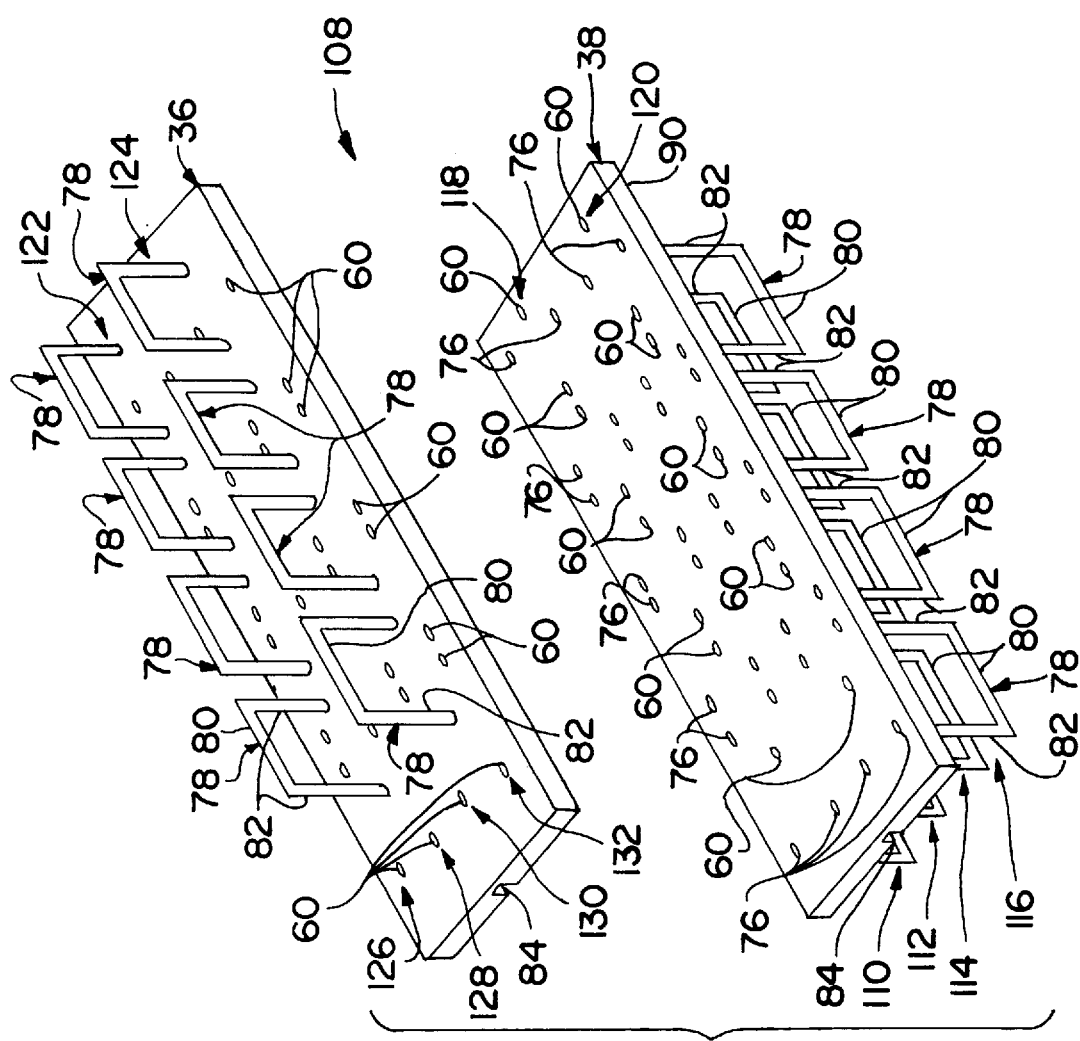
FIG. 10 is a perspective view of another modified staple cartridge according to the present invention.

The modified surgical staple cartridge 108 shown in FIG. 10 is similar to the surgical staple cartridge 30 depicted in FIG. 1 but with upper and lower cartridge bodies 36 and 38 formed as separate unconnected units and staples 78 carried by both cartridge bodies in opposed relation to apertures 60 formed in the other cartridge body. The cartridge bodies 36 and 38 are generally rectangular plates configured to fit within opposed jaws of a stapling instrument, for example along rails carried by the jaws. Lower cartridge body 38 carries four rows 110, 112, 114 and 116 of staples 78, each having four staples with cross members 80 spaced below the outer face 90 of the lower cartridge body 38 and legs 82 of the staples recessed within openings 76 formed in the lower cartridge body to protect the tissue penetrating tips of the legs. Two rows 118 and 120 of spaced apertures 60 are formed in the lower cartridge body 38 between innermost and outermost pairs of staple rows 112, 114, 110 and 116 and are aligned longitudinally with interstices between legs 82 of individual staples 78 carried by the lower cartridge body. Upper cartridge body 36 carries two rows 122 and 124 of staples 78 in opposed relation to apertures 60 formed in the lower cartridge body 38 and four rows 126, 128, 130 and 132 of apertures 60 are formed in the upper cartridge body 36 for receiving the tissue penetrating legs 82 of the staples carried by the lower cartridge body 38. Grooves 84 are formed in opposed relation along respective central longitudinal axes of the opposed cartridge bodies 36 and 38 and are configured to facilitate separation of the surgical staple cartridge 108 between rows of staples.

FIG. 11 illustrates yet another modification of the surgical staple cartridge of the present invention wherein the modified surgical staple cartridge 134 is configured to fit within curved jaws of a stapling instrument. The modified surgical staple cartridge 134 includes a single cartridge body 136 of generally rectangular shape carrying two coextensive and longitudinally aligned rows 138 and 140 of staples 78. Each staple row includes six staples 78 having cross members abutting an outer face 90 of the cartridge body and staple legs 82 extending perpendicularly from opposite ends of the cross members through openings in the cartridge body 136. Relief cuts 142 are formed perpendicular to the longitudinal axis of the surgical staple cartridge between adjacent staples and extend partway across the cartridge body in a transverse direction to form cartridge body segments joined by a thin band of material along a transverse edge of the cartridge body. Pairs of spaced apertures 60 are formed between the staples 78 of each segment and can be used in conjunction with an opposed cartridge body, such as the cartridge body shown in phantom at 146 in FIG. 11, for receiving tissue penetrating legs of staples carried by the phantom cartridge body 146, or the apertures 60 in the cartridge body 136 can be used as a line of weakening to facilitate separation of the cartridge body between rows of staples when only a single cartridge body is employed.

Deployment of the surgical staple cartridge 134 in a curved jaw 147 of a stapling instrument is depicted in FIG. 12, wherein the jaw includes a curved channel 148 of generally rectangular cross-section for retaining the cartridge body segments and shallow grooves 150, 152 and 154 formed along a bottom wall of the channel to provide clearance for portions of the staples 78 protruding from the outer face of the cartridge body. The surgical staple cartridge 134 is advanced distally into the jaw 147 with the thin band connecting the cartridge body segments on the side facing the center of curvature of the jaw so that as the surgical staple cartridge is advanced along the channel the relief cuts 142 separating the cartridge body segments will widen at an outer transverse edge of the cartridge body forming wedge-shaped spaces between the segments and allowing the surgical staple cartridge 134 to conform to the curvature of the jaw. Once positioned within the jaw, the modified surgical staple cartridge 134 will operate in the manner previously described. Also, if the staple cartridge 134 is positioned in one jaw of the stapler in opposed relation to anvils (not shown) formed in an opposed jaw, stapling of tissue held between the jaws can be accomplished without the use of a second cartridge body.

Figure 13:
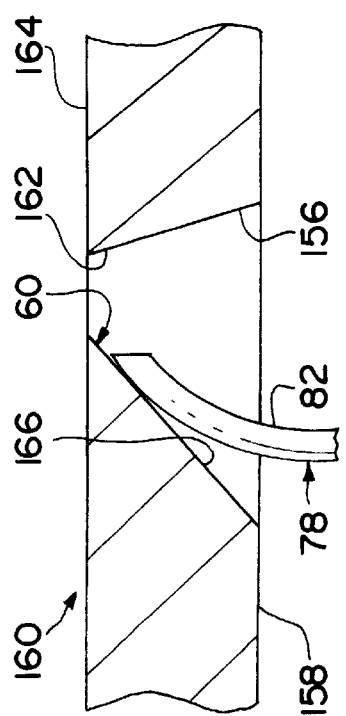
FIG. 13 is a fragmentary side view, partly in section, of a modified aperture for the staple cartridge according to the present invention.

Another modification of the surgical staple cartridge of the present invention is shown in FIG. 13, wherein the modified surgical staple cartridge 160 has apertures 60 similar to those previously described but defining large openings 156 along an inner face 158 of the cartridge body and tapering to relatively smaller openings 162 along an outer face 164 of the cartridge body. The apertures making up a given pair opposite tissue penetrating legs of a staple are tilted toward or away from one another to form angled camming surfaces 166 for bending the tissue penetrating legs 82 of a staple 78 as the legs pass through the apertures.

Figure 14:
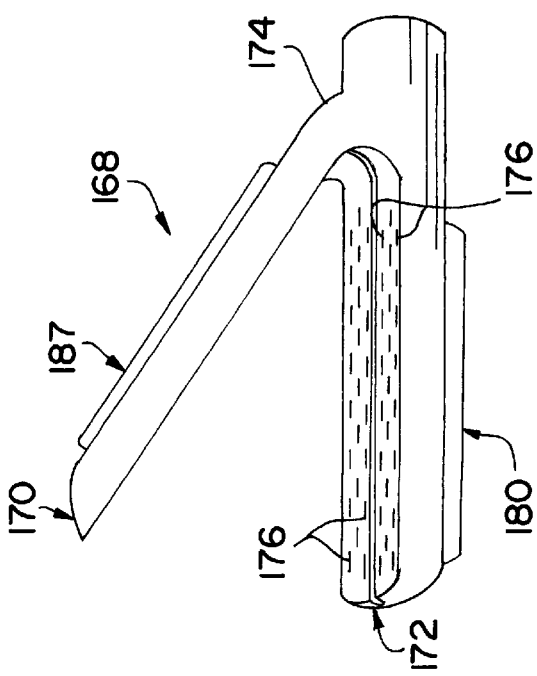
FIG. 14 is a perspective view of still another modified staple cartridge according to the present invention.
Figure 15:
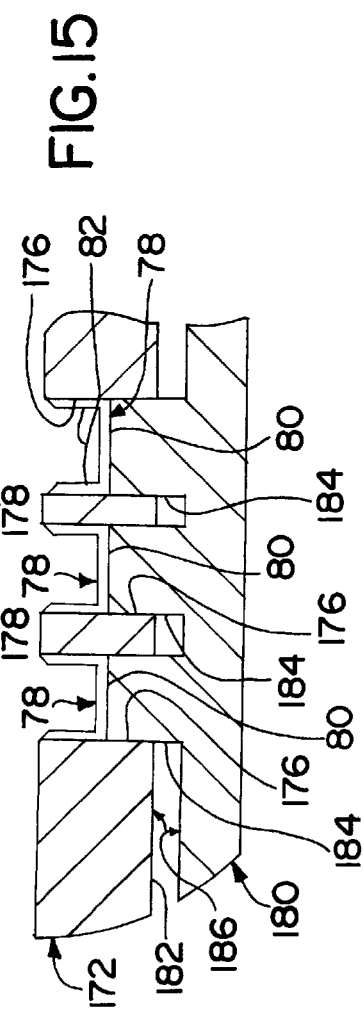
FIG. 15 is an enlarged fragmentary view, partly in section, of the staple cartridge of FIG. 14.

The surgical staple cartridge 168 shown in FIGS. 14 and 15 is configured to apply surgical staples to anatomical tissue without the cartridge bodies being fastened to the tissue. The modified surgical staple cartridge 168 includes upper and lower cartridge bodies 170 and 172 configured to fit within jaws of a stapling instrument, such as the instrument shown in FIG. 16 and described below. The cartridge bodies are joined at 174 by a hinge and are normally biased apart. As best seen in FIG. 15, the lower cartridge body 172 includes a plurality of pockets or slots 176 arranged in rows and configured to carry staples 78 with tissue penetrating legs 82 of the staples facing curved indents or anvils 178 formed in the upper cartridge body 170. The slots 176 extend completely through the lower cartridge body 172 and are preferably rectangular in shape to frictionally hold the staples 78.

A cam bar 180 extends longitudinally alongside an outer face 182 of the lower cartridge body 172 and carries a plurality of staple driving protrusions 184 which extend perpendicularly from the bar into the slots 176 to engage staple cross members 80 disposed within the slots. The cam bar 180 and lower cartridge body 172 are separated by a gap 186 allowing upward movement of the cam bar relative to the cartridge body in order to drive the staples 78 from slots 176 into anvils 178. Slots can also be formed in upper cartridge body 170 in opposition to anvils formed in the lower cartridge body 172 if complementary stapling from both sides of the anatomical tissue is desired; and, accordingly, a second cam bar 187 is shown spaced above the upper cartridge body 170 for driving staples from slots formed in the upper cartridge body.

Use of the surgical staple cartridge 168 for applying staples to anatomical tissue involves holding the staple cartridge between jaws of a surgical stapler and positioning the upper and lower cartridge bodies 170 and 172 on opposite sides of the anatomical tissue to be stapled. When jaws of the stapling instrument are closed around the surgical staple cartridge 168, cartridge bodies 170 and 172 are clamped against the anatomical tissue and cam bar 180 is moved toward the lower cartridge body 172. Movement of the cam bar 180 towards the lower cartridge body 172 causes the staple driving protrusions 184 to move upward within slots 176 driving the staples 78 out of the slots 176. As the staples 78 are driven out of slots 176, the legs 82 of the staples penetrate through the anatomical tissue held between the cartridge bodies and are received by the anvils 178 formed in the upper cartridge body 170. Anvils 178 crimp or bend the legs 82 of the staples against the anatomical tissue to hold the tissue in compression. Staples 78 in each row are preferably closely spaced and, when coupled with closely spaced staples in an adjacent row, prevent seepage of bodily fluids between rows of staples. Staggering adjacent rows of staples and delivering staples from opposite sides of the anatomical tissue are also preferred methods of providing a seal across anatomical tissue.

Unlike the staple cartridges previously described, surgical staple cartridge 168 remains with the stapling instrument after application of the staples to anatomical tissue. In the case of the surgical staple cartridge 168 being formed of bioabsorbable materials, the cartridge can be ejected from between the jaws of the stapling instrument and left within the body to be absorbed. In the case of the surgical staple cartridge 168 being made of non-bioabsorbable materials, the staple cartridge can be retrieved at any point during or after the surgical procedure.

Figure 17:
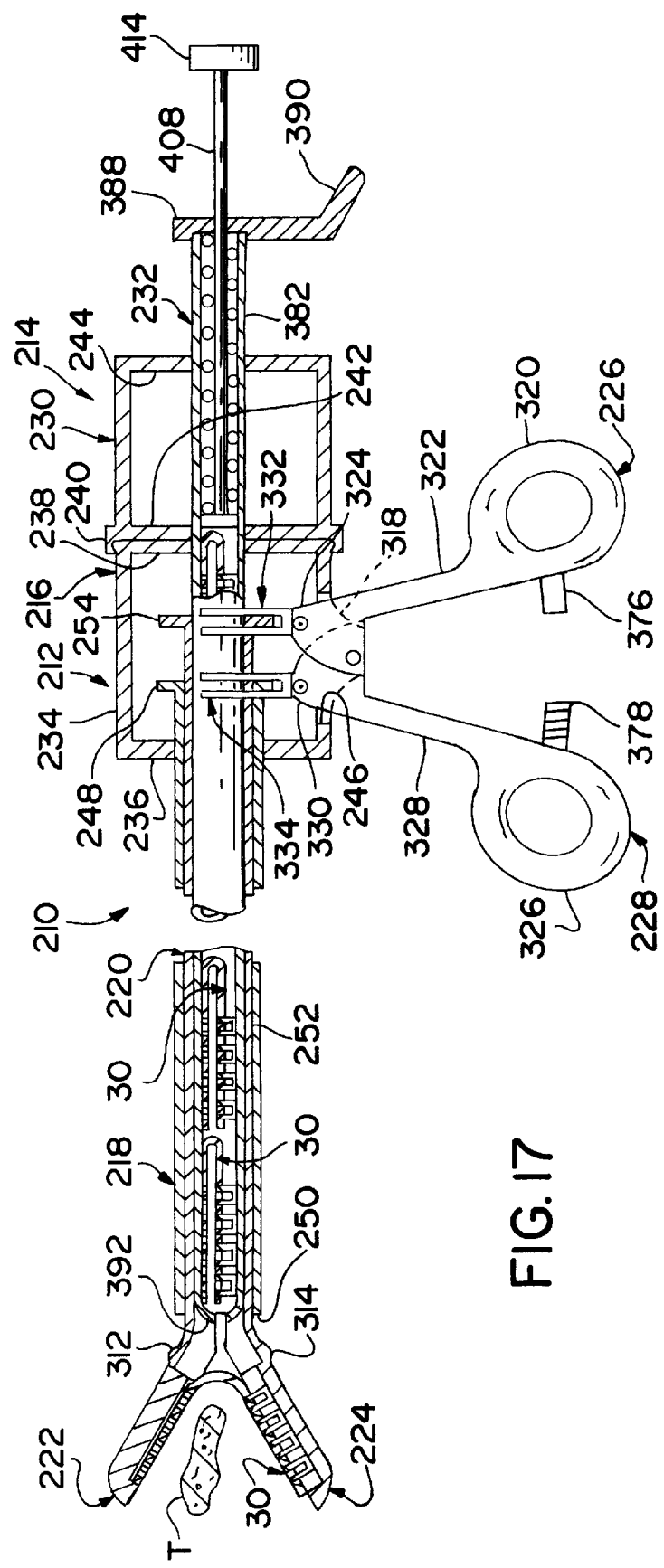
FIG. 17 is a broken side view, partly in section, of the surgical stapling instrument of FIG. 16.

The surgical stapling instrument or stapler 210 according to the present invention, as shown in FIGS. 16 and 17, includes a forceps unit 212 and an operating unit 214. Forceps unit 212 includes a housing 216, an outer tubular member 218 extending distally from the housing 216, an intermediate tubular member 220 telescopically fitted within the outer tubular member 218 and terminating distally in a pair of opposed jaws 222 and 224 and a pair of handles 226 and 228 extending from the housing at an angle relative to the longitudinal axis of the instrument. Operating unit 214 includes a hub 230 releasably coupled with the housing 216 and carrying an inner member 232 at least partly telescopically fitted within the intermediate tubular member 220.

As best seen in FIG. 17, housing 216 is generally tubular with a cylindrical sidewall 234 and front and rear walls 236 and 238 closing opposite ends of the cylindrical sidewall 234. A rear portion of the cylindrical sidewall 234 is externally threaded, keyed or otherwise configured to receive an internally threaded, keyed or cooperatingly configured sleeve or ring 240 carried by the cylindrical hub 230. Hub 230 has front and rear end caps 242 and 244 and can be mated with or separated from housing 216 by rotation for example; and when mated with housing 216, the front end cap 242 abuts housing rear wall 238. A slotted opening 246 is formed in the cylindrical sidewall 234 of housing 216 and extends longitudinally between the front and rear walls 236 and 238 of the housing to permit handles 226 and 228 to pass therethrough.

Outer tubular member 218 is open at both ends and extends through an opening in the housing front wall 236 to terminate proximally at a transverse flange 248 disposed between front wall 236 and rear wall 238 of the housing. Distal end 250 of outer tubular member 218 can be blunt as shown, tapered, beveled or chamfered as desired or have any other suitable distal configuration.

Intermediate member 220 includes a tubular body 252 telescopically fitted within the outer tubular member 218. The tubular body 252 terminates proximally at a transverse flange 254 disposed within the housing 216 between the outer tubular member flange 248 and housing rear wall 238; and, as best seen in FIGS. 18–22, a distal end of tubular body 252 is split longitudinally to form integral one-piece jaws 222 and 224 in opposed relation. Jaws 222 and 224 are normally biased apart as shown and define opposed semi-cylindrical recesses 256 and 258 for carrying jaw inserts 260 and 262. Jaw inserts 260 and 262 can be permanently or removably secured within the semicylindrical recesses using adhesives, detents, or any other suitable means or can be formed with jaws 222 and 224 as an integral one-piece construction.

Referring to FIGS. 19 and 20, lower jaw insert 262 defines a generally rectangular cavity 264 bounded by a bottom wall 266, a front side wall 268 and a pair of laterally spaced side walls 270 and 272. Top and back ends of the cavity 264 opposite the bottom and front walls 266 and 268 are open. A central longitudinal groove 274 is formed in the bottom wall 266 of the cavity and is configured to accommodate a cam bar or cutting blade for example. Three longitudinal grooves 276, 278 and 280 are formed in the bottom wall 266 to one side of the central groove 274 and another group of three longitudinal grooves 282, 284 and 286 are also formed in the bottom wall of the cavity on the other side of the central groove 274. Longitudinal grooves 276, 278, 280, 282, 284 and 286 are configured to slidingly receive portions of the staples spaced below a lower cartridge body 38 as shown in phantom in FIG. 20. Lower cartridge body 38 is suspended directly above cavity 264 atop tissue penetrating legs of the staples.

Referring to FIGS. 21 and 22, upper jaw insert 260 defines a generally rectangular cavity 288 bounded by a bottom wall 290, a front side wall 292 and a pair of laterally spaced side walls 294 and 296. Top and back ends of the cavity 288 opposite the bottom and front walls 290 and 292 are open. A central longitudinal groove 298 and six longitudinal grooves 300, 302, 304, 306, 308 and 310 arranged in groups of three on opposite sides of the central groove are formed in the bottom wall 290 of the cavity 288 in opposed relation to the central longitudinal groove 274 and six longitudinal grooves 276, 278, 280, 282, 284 and 286 formed in the lower jaw insert. As shown in phantom at 36 in FIG. 22, upper cartridge body 36 fits within the rectangular cavity 288 with apertures 60 in the upper cartridge body aligned with the six longitudinal grooves 300, 302, 304, 306, 308 and 310.

Referring again to FIG. 18, wedge-like cams 312 and 314 are formed on respective exterior surfaces of jaws 222 and 224 and are distally spaced from outer member distal end 250 when jaws 222 and 224 are open. Cams 312 and 314 taper toward bends joining each jaw with the tubular body 252.

Tubular body 252 of intermediate member 220 is preferably formed with jaws 222 and 224 as an integral one-piece part using a resilient medically-acceptable material such as a stainless steel or plastic having suitable elastic properties for normally biasing the upper and lower jaws 222 and 224 apart while permitting the jaws to be moved towards one another in response to axial forces acting on the jaws and/or cams as a result of relative movement between the outer tubular member 218 and intermediate member 220.

Referring again to FIG. 17, handles 226 and 228 are conventional and extend through slotted opening 246 in the side wall 234 of housing 216. Each handle is pivotally mounted on a bolt, dowel or pin 316 secured to a mounting plate 318 extending outward from side wall 234 along an edge of slotted opening 246. In a preferred embodiment, a torsion spring (not shown) is coiled around pin 316 and connected between handles 226 and 228 to bias the handles toward one another such that jaws 222 and 224 are normally held in a partly closed condition as will be explained further below with reference to FIG. 28. Proximal handle 226 includes a finger loop 320 configured to accommodate one or more fingers of the user and a shank 322 connecting the finger loop with a flattened end portion 324. End portion 324 extends into housing 216 towards intermediate member flange 254 through slotted opening 246 and protrudes distally from shank 322 to pivotally mount pin 316. Distal handle 228 includes a finger loop 326 configured to accommodate one or more fingers of the user and a shank 328 connecting the finger loop with a flattened end portion 330 and sliding contact with blade portion 324 and extending into housing 216 towards outer member flange 248 through slotted opening 246 and protruding proximally from shank 328 to pivotally mount pin 316.

Figure 24:
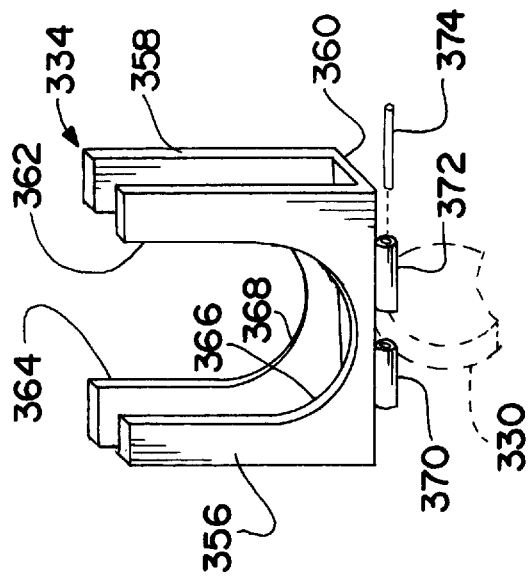
FIGS. 23 and 24 are perspective views of brackets for use with the surgical stapling instrument of FIG. 16.
Figure 23:
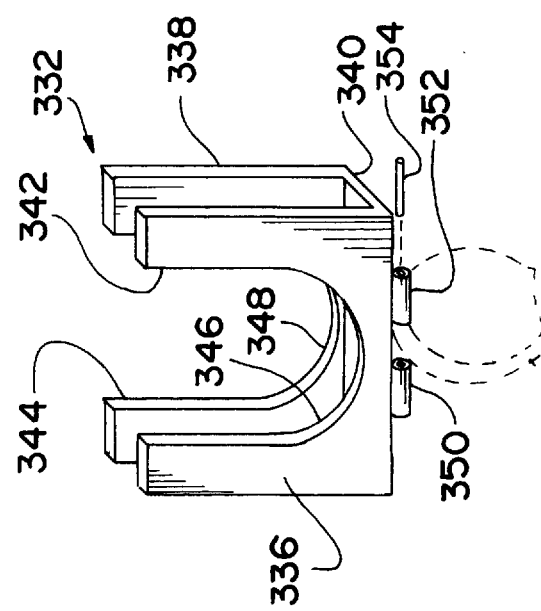

Handles 226 and 228 are coupled with intermediate and outer members 220 and 218 using brackets 332 and 334, respectively. As best seen in FIG. 23, bracket 332 is generally U-shaped and includes forward and rearward walls 336 and 338 spaced to accommodate intermediate member flange 254 therebetween and a bend portion 340 joining the forward and rearward walls. Vertical notches 342 and 344 with semicircular bottoms 346 and 348 are formed in walls 336 and 338 with the semicircular bottoms being concentrically aligned for allowing passage of the intermediate and inner members 220 and 218 through bracket 332 while clamping intermediate member flange 254 between the forward and rearward walls of the bracket. A pair of tubular bosses 350 and 352 are mounted underneath bracket 332 in axial alignment and spaced to accommodate the flattened end portion 324 of handle 226 therebetween. A pin 354 pivotally connects the blade portion 324 with bosses 350 and 352. Bracket 334, shown in FIG. 24, is similar to bracket 332 and includes forward and rearward wall 356 and 358 joined by a transverse bend 360, notches 362 and 364 with semicircular bottoms 366 and 368 for accommodating outer and intermediate members 218 and 220, and bosses 370 and 372. End portion 330 of distal handle 228 fits between bosses 370 and 372 and is rotatably held therebetween by pin 374.

Referring again to FIG. 17, mating protrusions 376 and 378 are carried at opposed locations on finger loops 320 and 326 to lock handles 226 and 228 together when rotated towards one another a predetermined angular distance corresponding to a desired resultant linear separation between brackets 332 and 334. Mating protrusions 376 and 378 are shown having serrated inside surfaces for ratcheting engagement, but can have any other configuration to mate frictionally or latch together when engaged.

Figure 25:
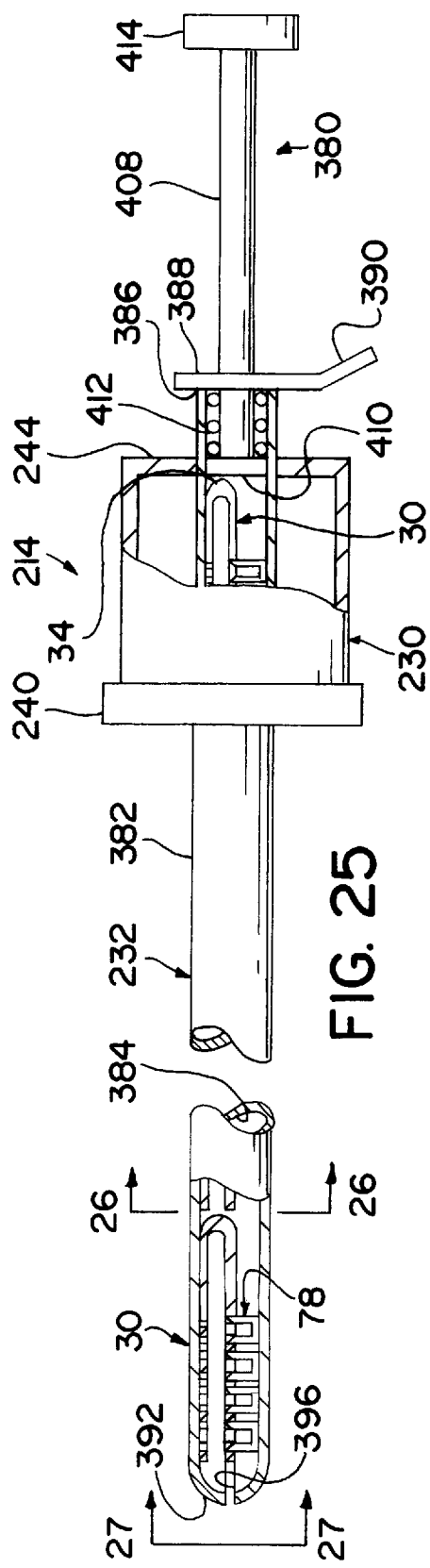
FIG. 25 is a broken side view, partly in section, of a staple cartridge magazine for use as an operating unit with the surgical stapling instrument of FIG. 16.
Figure 28:
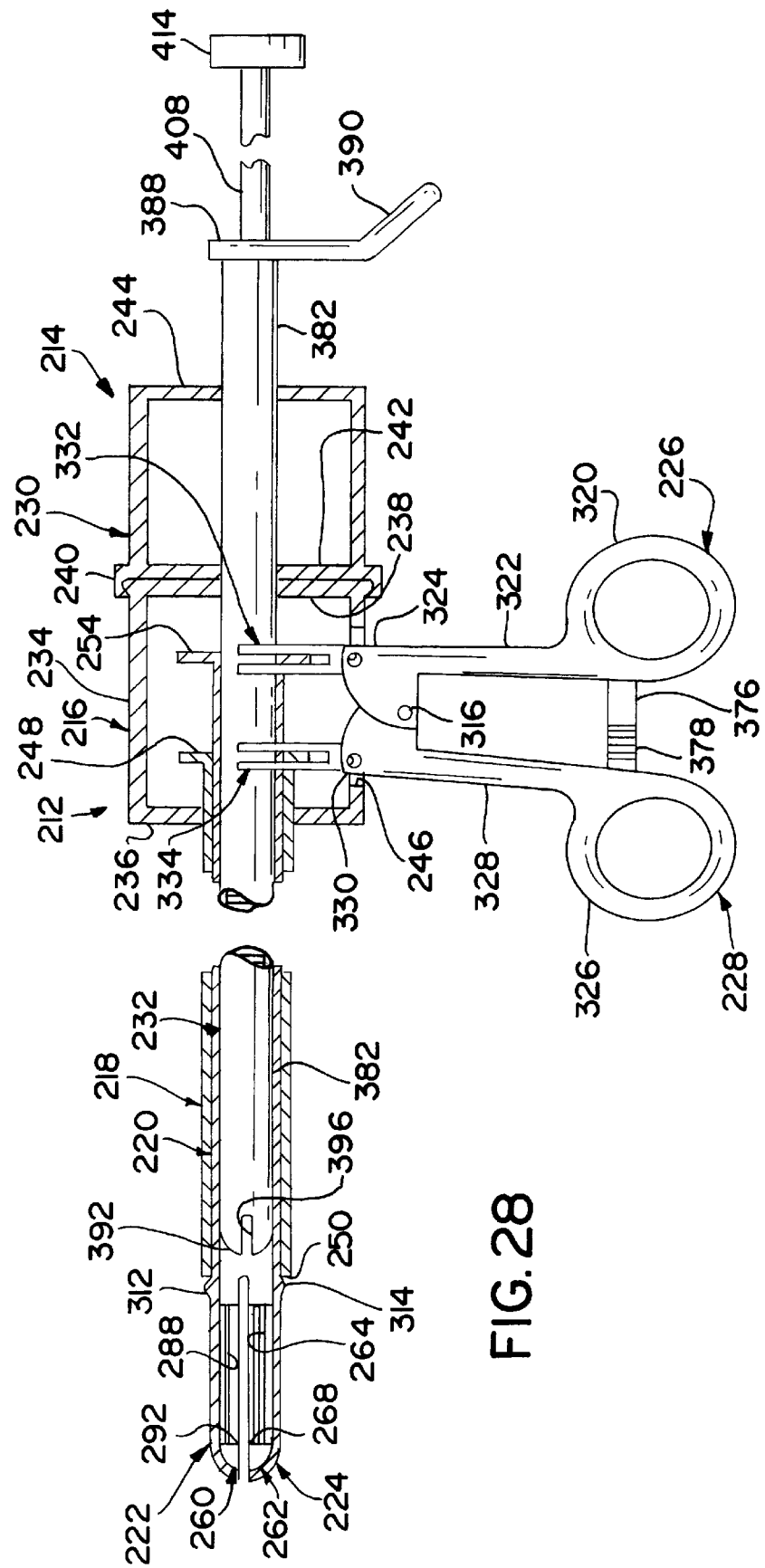
FIGS. 28 and 29 are broken side views, partly in section, illustrating use of the surgical stapling instrument of FIG. 16.

The surgical stapling instrument 210 can be provided as shown in FIG. 28 with the operating unit hub 230 attached to the forceps unit housing 216, or the operating unit 214 can be provided separately as shown in FIG. 25 so that the hub 230 can be threadedly or otherwise fitted to the housing 216 by the user. The latter is particularly desirable where a number of operating unit hubs carrying various types of inner members are available, allowing the user to select an appropriate hub/inner member combination for the particular procedure to be performed.

Figure 26:
FIG. 26 is a cross-sectional view taken through line 26—26 in FIG. 25.
Figure 27:
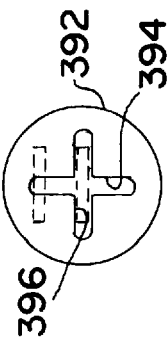
FIG. 27 is a front view of the operating unit of FIG. 25.

Referring now to FIGS. 25–27, operating unit 214 shown includes a hub 230 configured to mate with housing 216 of forceps unit 212, a hollow inner member 232 fixedly mounting the hub, a plurality of surgical staple cartridges 30 disposed within the inner member, and a surgical staple cartridge advancing mechanism 380. Inner member 232 includes a generally tubular elongate body 382 defining a rectangular channel 384 for storing a plurality of surgical staple cartridges 30. The tubular body 382 is closed at a proximal end 386 by an end wall 388 extending transversely beyond the tubular body to form a finger rest, flange or handle 390. As best seen in FIG. 27, distal end of the tubular body 382 forms a generally hemispherical cap 392 with orthogonal slits 394 and 396 extending radially outward from an apex of the cap to define resilient flaps or petals. Surgical staple cartridges 30 are arranged end-to-end within the rectangular channel 384 of the inner member behind the flaps of the hemispherical cap 392. Cartridge bodies 36 and 38 of each surgical staple cartridge 30 are closed part way so that the surgical staple cartridges can fit within the rectangular channel 384 of the inner member without the staples 78 carried by the cartridge bodies 38 being driven into the space between cartridge bodies 36 and 38. The flaps at the distal end of the inner member serve as resilient stops or abutment members for resisting distal movement of the surgical staple cartridges 30.

The advancing mechanism 380 includes a rod 408 extending through an opening in proximal end wall 388, a piston 410 mounted at a distal end of the rod, a bias member 412 and a knob or handle 414 at a proximal end of the rod 408. Piston 410 is generally rectangular and is configured to slide within channel 384. Bias member 412 includes a helical coil spring disposed around rod 408 and held in compression between the piston 410 and the proximal end wall 388 to normally bias the piston in a distal direction into abutting contact with the hinge 34 of the surgical staple cartridge 30 nearest the proximal end of the channel 384. Since the surgical staple cartridges 30 are arranged end-to-end, cartridge bodies 36 and 38 of each surgical staple cartridge will bear against the hinge 34 of the next distally located staple cartridge so that all of the surgical staple cartridges 30 are advanced distally in response to the distal bias of spring 412. Cartridge bodies 36 and 38 of the surgical staple cartridge 30 nearest the distal end of the tubular body 382 abut the hemispherical cap 392 of the tubular member and are restrained from further distal movement by the flaps.

If the operating unit 13 is provided separately, assembly of the stapling instrument 210 requires that inner member 232 carried by the hub 230 be inserted through an opening in the rear wall 238 of the housing 216 and advanced distally into intermediate member 220 until ring 240 of the hub meets the threaded or keyed portion of the housing sidewall 234. Hub 230 can then be mated to housing 12 by positioning the hub against the housing and rotating the hub until the front end cap 242 of the hub is disposed proximate housing rear wall 238.

In the assembled condition, shown in FIG. 28, the hemispherical distal end 392 of the inner member 232 terminates slightly behind jaws 222 and 224 so that a surgical staple cartridge 30 ejected from the distal end of the inner member will be received between the jaws. Jaws 222 and 224 are preferably partly closed prior to receiving a surgical staple cartridge 30 in order to capture the surgical staple cartridge and to align the grooves formed in the jaw inserts with staples 78 sticking out from the bottom of the surgical staple cartridge. As mentioned previously, jaws 222 and 224 are normally biased apart as shown in FIG. 18; however, handles 226 and 228 are preferably biased together so that outer and intermediate member flanges 248 and 254 of the stapling instrument 210 are suitable spaced apart to cause the distal end 250 of outer tubular member 218 to slide distally over jaws 222 and 224 in order to partly close the jaws. More specifically, movement of handles 226 and 228 toward one another under the influence of a bias member, such as a torsion spring connected between the handles, causes brackets 332 and 334 carried at the opposite end of handles 226 and 228 to be pivoted away from one another about pin 316. The longitudinal component of the pivotal movement of brackets 332 and 334 moves outer and intermediate member flanges 248 and 254 apart. Any transverse component of the bracket movement is accommodated by vertical sliding of the bracket walls against intermediate and outer member flanges 248 and 254. Movement of outer and intermediate member flanges away from one another causes the outer member distal end 250 to slide distally over jaws 222 and 224 tending to cam the jaws toward one another. At this point, jaws 222 and 224 are partly closed, i.e., separated by a small gap, outer member distal end 250 abuts cams 312 and 314 on opposite sides of the partly closed jaws and mating protrusions 376 and 378 can be in close contact as shown or engaged to prevent inadvertent movement of the jaws.

Figure 29:
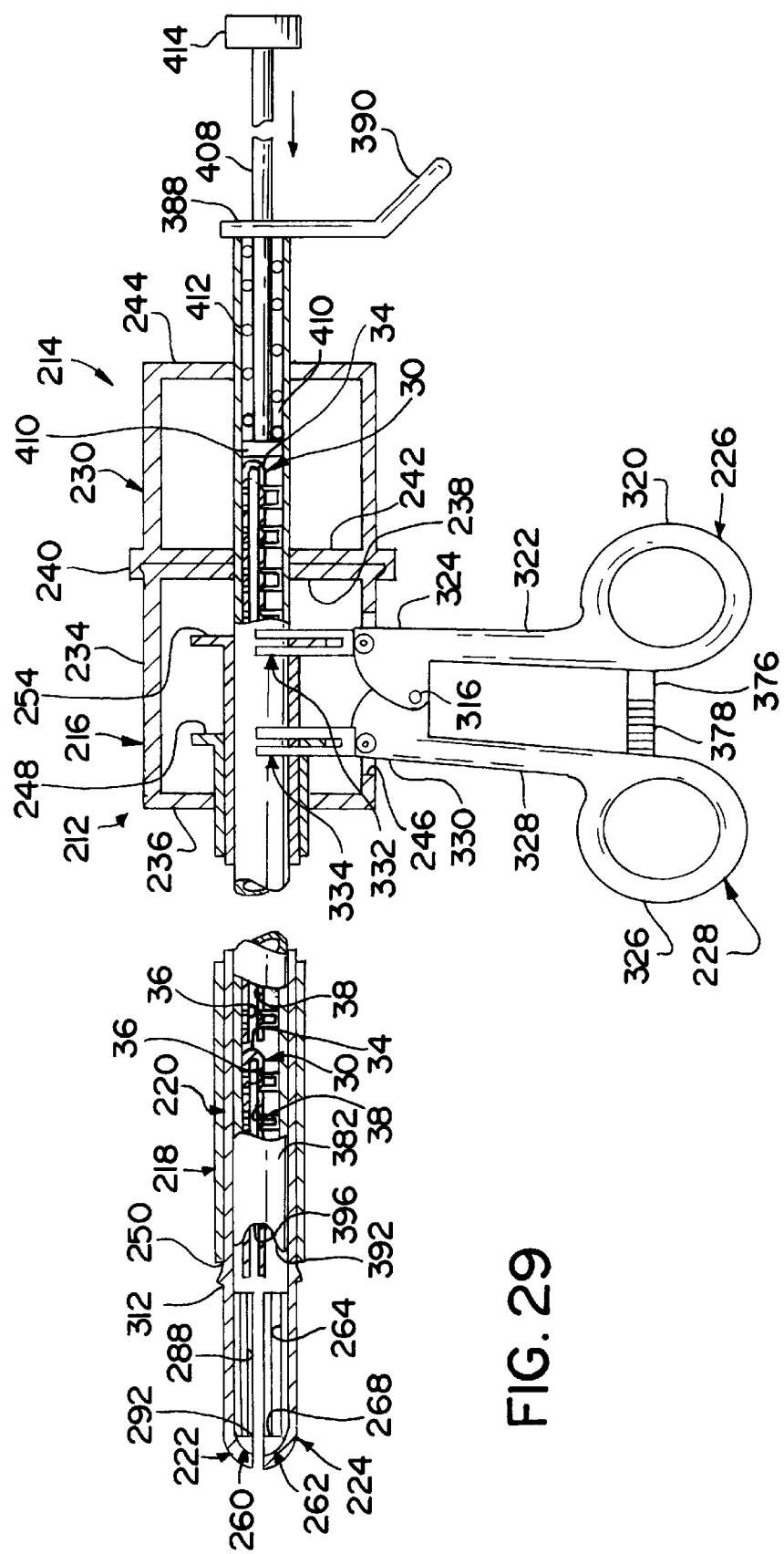

A surgical staple cartridge 30 is positioned between the partly closed jaws 222 and 224 by depressing handle 414 at the proximal end of rod 408 toward proximal end wall 388. Since the inner member 232 is fixed relative to the hub 230, depression of the handle 414 causes the rod 408 and piston 410 to move distally within the rectangular channel 384 formed inside the tubular member 382. Piston 410 is already biased against the surgical staple cartridge 30 nearest the proximal end of the instrument and, since ends of the surgical staple cartridges contact one another, all of the surgical staple cartridges are normally distally biased within the tubular body of the inner member with the distalmost surgical staple cartridge 30 abutting the hemispherical distal end 392 of the tubular body. Further distal movement of the piston 410 as a result of the handle 414 being depressed urges the distalmost surgical staple cartridge 30 past the flaps of the hemispherical cap 392, as shown in FIG. 29, and into the cavities 288 and 264 formed in upper and lower jaw inserts 260 and 262. Upper cartridge body 36 of the distalmost surgical staple cartridge 30 is aligned with an open end of upper cavity 288 and the portions of staple 78 that stick out from the lower cartridge body 38 are aligned with grooves 276, 278, 280, 282, 284 and 286 formed in the bottom wall of the lower cavity 264.

Figure 30:
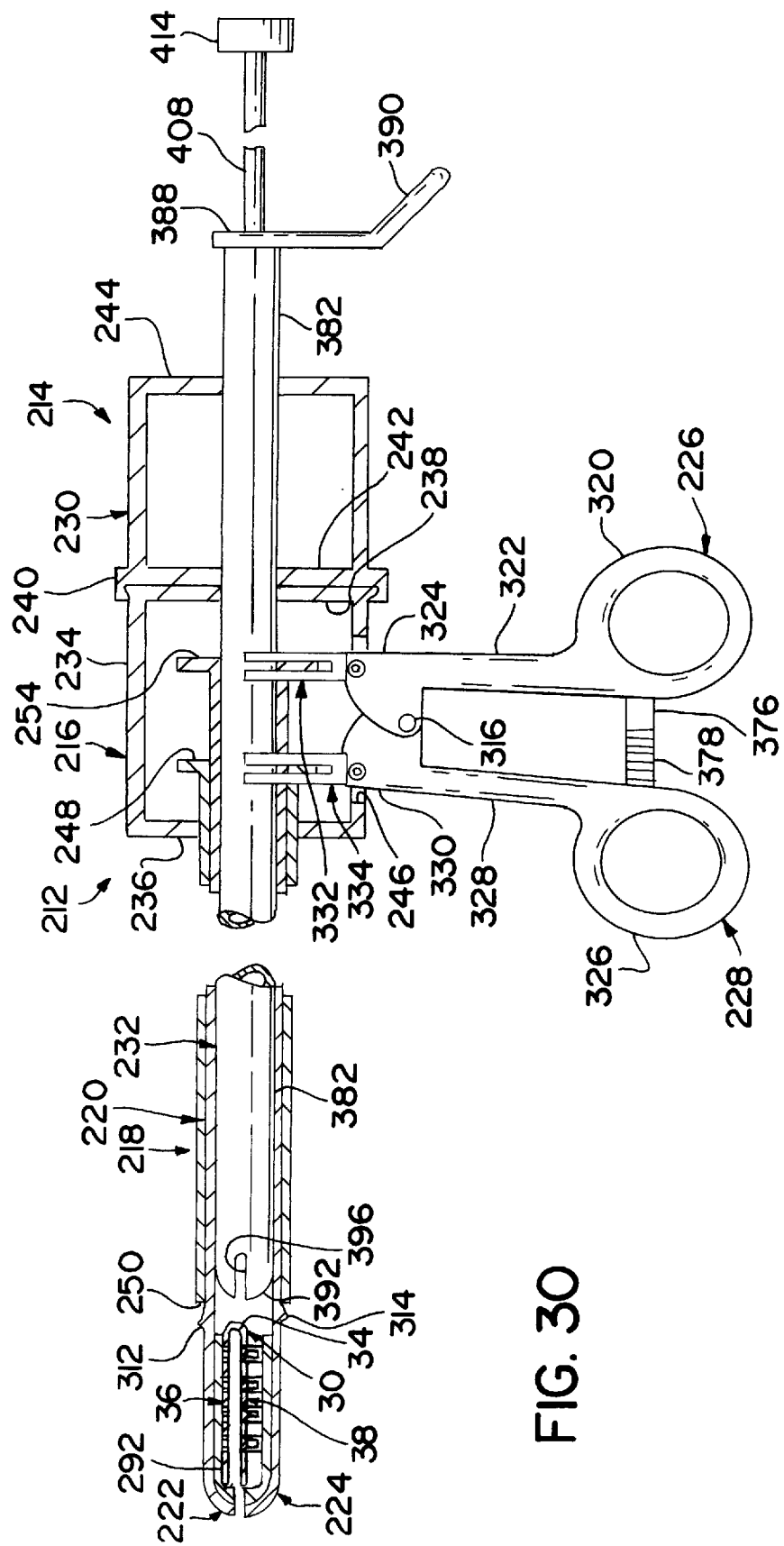
FIGS. 30 and 31 are broken and fragmentary side views, respectively, further illustrating use of the surgical stapling instrument of FIG. 16.

Referring now to FIG. 30, handle 414 at the end of rod 408 is depressed until the distalmost surgical staple cartridge 30 is positioned between jaws 222 and 224. Upper cartridge body 36 of the surgical staple cartridge 30 is received within upper cavity 264 as handle 414 is depressed and, when the surgical staple cartridge is properly positioned, will abut the front wall 292 of the cavity preventing further distal movement of the surgical staple cartridge and providing a tactile signal at the proximal end of the rod 408 that the surgical staple cartridge 30 is fully advanced. Upper cartridge body 36 is seated at the bottom of cavity 288 in the upper forceps jaw 222 above grooves 300, 302, 304, 306, 308 and 310 when the surgical staple cartridge is fully advanced or deployed. Lower cartridge body 38 is elevated above the bottom of cavity 264 and the lower forceps jaw 224 with the cross-member end of staple 78 extending downward from the lower cartridge body 38 into grooves 276, 278, 280, 282, 284 and 286. Hinge 34 of the deployed surgical staple cartridge is spaced distally of the hemispherical cap 392 and the flaps formed by the radial slits in the hemispherical cap close behind the distalmost surgical staple cartridge 30 to prevent the next surgical staple cartridge from being ejected from the inner member 232 inadvertently.

Figure 31:
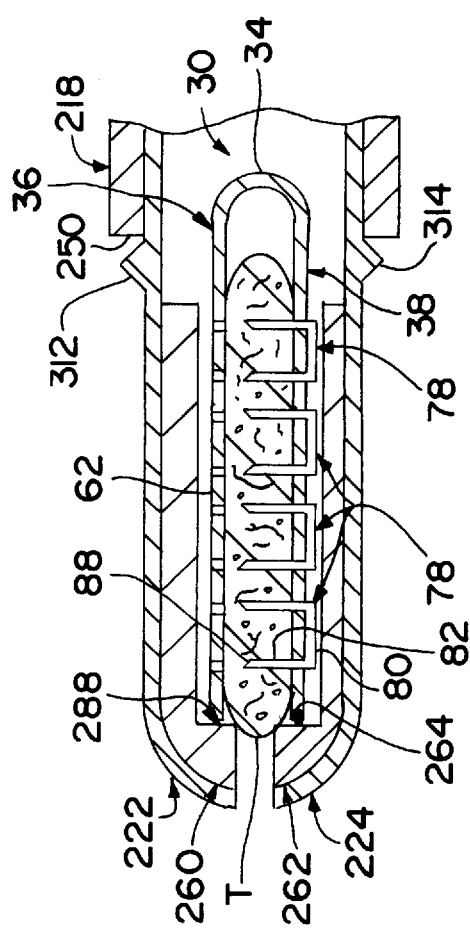

Stapling of anatomical tissue with the stapling instrument 210 involves opening jaws 222 and 224 with a surgical staple cartridge 30 held therebetween, positioning opposed cartridge bodies 36 and 38 of the surgical staple cartridge 30 around the anatomical tissue and closing the jaws to compress the cartridge bodies against the tissue. Jaws 222 and 224 of the forceps unit are opened by exerting finger pressure on finger loops 320 and 326 to spread the loops apart as shown in FIGS. 16 and 17. Movement of finger loops 320 and 326 away from one another causes brackets 332 and 334 to be rotated towards one another around pin 316 and draws intermediate and outer member flanges 254 and 248 toward one another. Outer member distal end 250 slides proximally away from cams 312 and 314 on jaws 222 and 224 allowing the jaws to open under the influence of their own resilience. With jaws 222 and 224 in the open condition shown in FIG. 17, anatomical tissue T to be stapled is positioned between cartridge bodies 36 and 38 held between the jaws. When the anatomical tissue T is properly positioned, jaws 222 and 224 are closed around the tissue by releasing finger pressure from the handles 226 and 228 and/or drawing the handles toward one another to slide the outer tubular member 218 over the jaws as previously described. Cartridge bodies 36 and 38 are thus compressed against opposite sides of the anatomical tissue T and the force from tissue contact on the inner face 46 of the lower cartridge body 38 causes the lower cartridge body to recede into the cavity 264 in the lower forceps jaw 224 by sliding over legs 82 of the staple 78 toward the cross-members 80 seated within grooves 276, 278, 280, 282, 284 and 286. As lower cartridge body 38 slides down the staple legs 82, tissue penetrating tips 88 of the staple 78 are exposed along the inner face 46 of the lower cartridge body and are made to penetrate into the anatomical tissue T as shown in FIG. 31.

Figure 33:
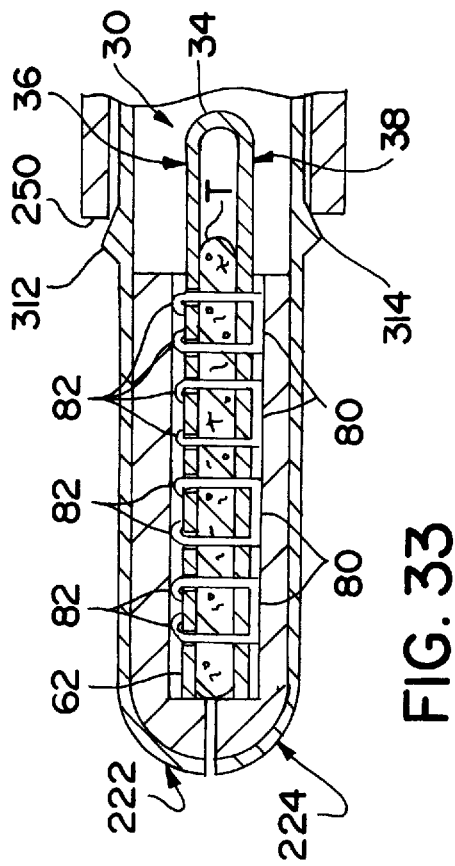
FIGS. 32 and 33 are broken and fragmentary side views, respectively, further illustrating use of the surgical stapling instrument of FIG. 16.
Figure 32:
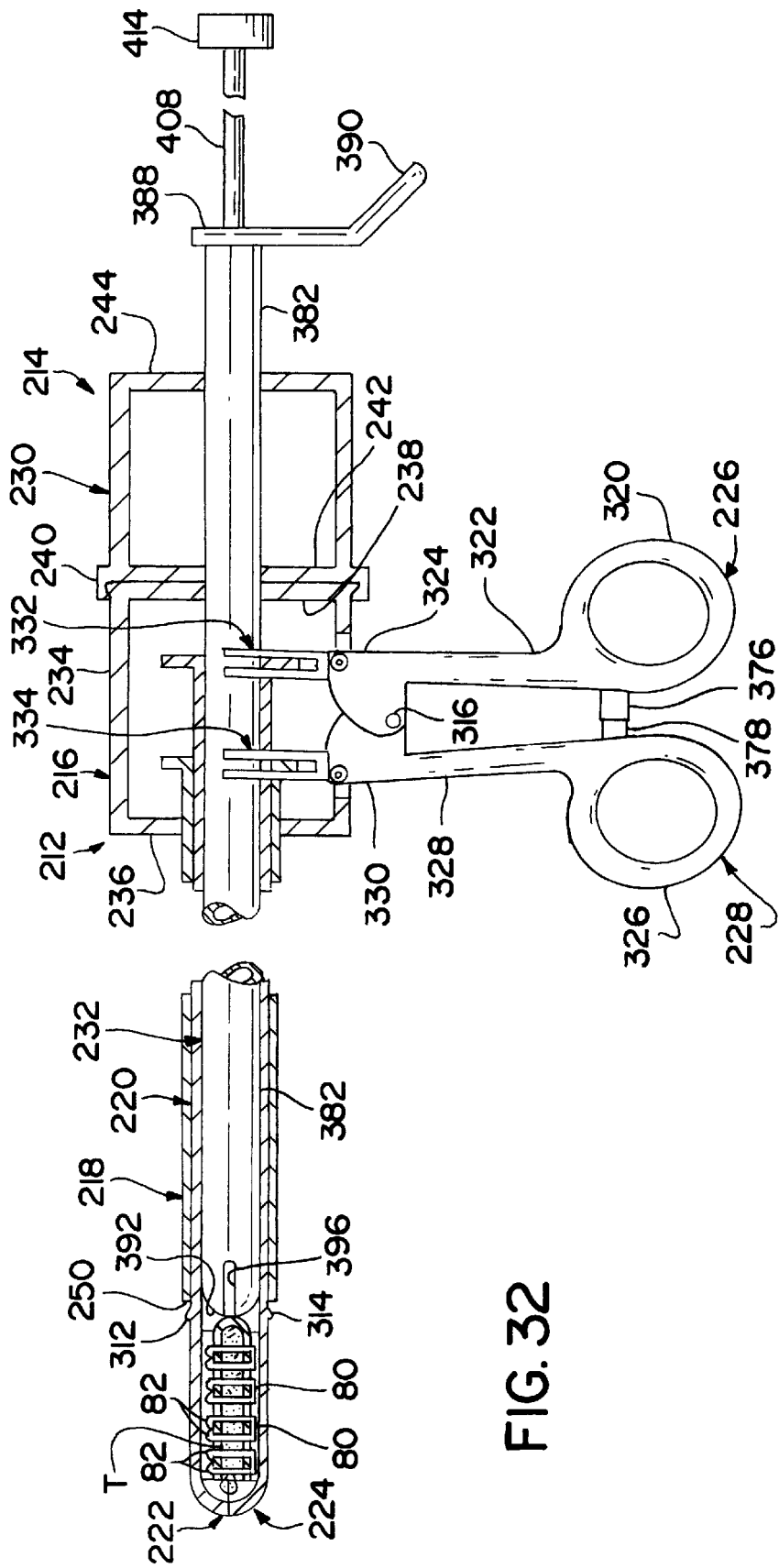

Staple legs 82 are driven through the anatomical tissue T by continued compression of the jaws 222 and 224 around the tissue. The jaws 222 and 224 are further compressed or closed more completely by drawing finger loops 320 and 326 towards one another until outer member distal end 250 slides distally over cams 312 and 314 to force the jaws into close contact with one another. Advancement of the outer member 218 over the cams 312 and 314 will result in greater compression of the tissue and will drive legs 82 into opposing apertures 60 formed in upper cartridge body 36 until the legs protrude from the outer ends of the apertures and are bent against the grooves 300, 302, 304, 306, 308 and 310 formed in the upper jaw insert as shown in FIGS. 32 and 33. The bent staple legs 82 bear against the outer face 62 of the upper cartridge body 36 to hold the anatomical tissue T in compression between the cartridge bodies.

When jaws 222 and 224 are opened, cartridge bodies 36 and 38 remain stapled to the anatomical tissue T creating an open space between the jaws for receiving the next surgical staple cartridge 30, which is advanced between the jaws and applied to anatomical tissue in the same manner as previously described. After all surgical staple cartridges 30 held within the inner member 232 have been fired, the inner member 232 can be reloaded, for example by unscrewing proximal end wall 388 and inserting new surgical staple cartridges 30 into the tubular body 382, or the operating unit, including the inner member 232, can be removed from the forceps unit 212 and a new operating unit having a full magazine of staple cartridges can be substituted for the spent operating unit. Replacement of operating unit 214 involves unscrewing the hub 230 from housing 216 and withdrawing the hub along with inner member 232 to permit a new operating unit hub carrying the same or a different type of inner member to be inserted for performing stapling or other functions, such as cutting, grasping, hooking, manipulating, dissecting, collecting tissue for biopsy, penetrating, injecting, creating suction, aspirating, irrigating, cauterizing, suturing, ligating, visualizing and illuminating. During substitution of operating units, the opening in the rear wall of the housing can be closed, for example, using a finger or conventional valves such as stopcock, flapper or trumpet valves, to help prevent loss of pneumoperitoneum in endoscopic procedures.

From the above, it will be appreciated that the stapling instrument of the present invention permits staples to be applied to anatomical tissue from multiple staple cartridges in succession without the need of having to withdraw the instrument from the surgical field. The staple cartridges can be formed of bioabsorbable materials and left within the body to eliminate the need for retrieving spent staple cartridges and, when stapled to the anatomical tissue, the cartridge bodies can serve as pressure plates to apply a more uniform pressure across the stapled tissue. It will also be appreciated that the surgical stapling instrument of the present invention eliminates the need for frequent withdrawal of stapling instruments from the surgical field to replace spent cartridges, that contact with a distal end of the surgical stapling instrument is minimized during loading and reloading procedures to reduce the risk of exposing medical personnel to body fluids, that the time required for reloading stapling instruments is reduced and that endoscopic procedures can be simplified by carrying out multiple functions with a single endoscopic instrument having a forceps unit that remains within an anatomical cavity and interchangeable operating units, one of which carries a plurality of staple cartridges and means for advancing the staple cartridges between jaws of the forceps unit.

Various bioabsorbable or biodegradable materials can be used to make the staple cartridges of the present invention with the composition determined by the rigidity or flexibility required. Generally, the bioabsorbable materials are thermoplastic polymers such as absorbable polymers and copolymers of poly-dioxane, lactide, glycolide and the like. Polyglycolic acid is disclosed in U.S. Pat. Nos. 3,463,158; 3,739,773 and 3,772,420. Suitable polylactic acids are disclosed in U.S. Pat. No. 3,636,956. Examples of absorbable polyesters are shown in U.S. Pat. Nos. 3,225,766 and 3,883,901. Absorbable cellulose glycolic acid ethers are shown in U.S. Pat. No. 2,764,159. Examples of suitable esters of alpha-cyanoacrylic acid are found in U.S. Pat. Nos. 3,527,841; 3,564,078 and 3,759,264.

The tubular member and jaws of the forceps unit of the present invention are preferably formed as an integral one-piece construction and can be movably disposed within an outer tubular member to permit sliding movement of the outer tubular member over the jaws. The outer member and tubular forceps member can be mounted by a housing and coupled using any suitable handle mechanism and linkages for producing relative movement between the jaws and the outer tubular member. It will be appreciated, however, that the surgical staple cartridges of the present invention can also be operated from between jaws of any type of forceps unit. The forceps unit housing and operating unit hub can have any configuration for being releasably coupled including threaded portions, detents, slots, latches or any other types of suitable connections. The housing and hub can be cylindrical as shown or have any other configuration in cross-section.

Jaws 18 and 20 of the present invention can be straight as shown or curved and can have integrally formed or removable inserts with configurations for grasping and holding tissue and objects such as needles. The inserts can have any combination or number of longitudinal grooves formed in the inserts for accommodating the surgical staple cartridges, blades, scissors, biopsy tools, needles, hooks, surgical clips or any other surgical implements. The grooves can extend part way to define stops or abutments limiting distal movement of the implements or can extend the complete length of the inserts to form openings or apertures at the distal end of the jaws to allow passage of the implements beyond the distal end of the jaws when the jaws are closed. The jaws can have any shape and cross-section when closed, including circular, elliptical, rectangular and polygonal configurations, and can have opposed arcuate portions for clamping tubular objects without compressing the objects.

The handles and linkages shown and described herein for sliding the outer member over the jaws are exemplary of the types of conventional handle mechanisms suitable for performing the function of closing the jaws; accordingly, the handles can have any configuration for producing relative movement between the outer and intermediate members such as, for example, two pivoted legs with finger loops and sliding brackets as shown, one fixed and one pivoted leg with finger loops, a fixed pistol grip and movable trigger member or resilient U-shaped members connected between outer and intermediate members. Moreover, the handles can have any orientation relative to the longitudinal axis of the instrument including, for example, substantially transverse orientations whereby the handles extend transversely from a sidewall of the housing or substantially longitudinal orientations whereby the handles extend longitudinally from a rear wall of the housing and are operated like a scissors. Suitable linkages include brackets with sliding motion, gears mounted on or between handles and the outer and intermediate members, pulleys and cords or any direct or indirect coupling mechanism. The intermediate and outer members can be frictionally fitted to maintain a current position by resisting relative movement, can be biased apart with a bias member such as a helical coil spring disposed around the intermediate member and held in compression between intermediate and outer member flanges, or can be biased together as desired.

Inner faces of the surgical staple cartridge bodies can be smooth as shown or provided with a knurled or diamond-shaped tread for gripping anatomical tissue when compressed together. Grooves can be formed longitudinally between adjacent rows of staples to facilitate cutting of the staple cartridges following application of the staples to anatomical tissue, or, when surgical staple cartridges without grooves are used, more than one surgical staple cartridge can be applied to the anatomical tissue in close proximity and a cut made between the surgical staple cartridges using conventional cutting implements. The cartridge bodies can be monolithic or composite and any number of rows of staples having any number of staples within a row can be carried by a cartridge body. Opposed cartridge bodies can be separate or hinged as desired, and when hinged, the hinges can have any configuration including curved, V-shaped or laterally spaced double or multiple hinge configurations. The staples can have any number of legs or cross-members and can be made of any suitable medically acceptable material. Also, the legs of the staples can be recessed or protrude from openings in the cartridge bodies as desired.

The staple cartridge advancing mechanism shown and described herein for positioning surgical staple cartridges between the jaws of a forceps unit are exemplary of the types of advancing mechanisms suitable for performing the function of advancing the staple cartridges. It will be appreciated that the surgical staple cartridges can also be advanced using plungers, pusher bars or any other type of advancing mechanism. It will also be appreciated that multiple staple cartridges can be advanced side by side between jaws of a forceps unit and applied simultaneously to anatomical tissue to create separate rows of staples in anatomical tissue to be transected for example.

The components of the stapling instrument of the present invention can be made of any suitable, medical grade materials to permit sterilization for reuse or for single patient use. The components can be made of multiple parts of various configurations and materials to reduce cost. The forceps unit and/or the operating unit can have various valves, stopcocks and seals therein to control fluid flow therethrough, and conventional detent mechanisms can be used to connect or latch the hub with the housing when the forceps unit and the operating unit are assembled.

The features of the various embodiments described above can be combined in any manner desired dependent upon the operational requirements and complexity of the surgical stapling system.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical staple cartridge comprising
a pair of generally coextensive cartridge bodies adapted to fit within opposed jaws of a surgical stapler;
a hinge connecting said cartridge bodies;
a staple having ductile tissue penetrating legs, said staple being carried by a first of said cartridge bodies; and
means formed in a second of said cartridge bodies for receiving said tissue penetrating legs of said staple when said staple is driven through anatomical tissue.

2. A staple cartridge as recited in claim 1 wherein said cartridge bodies are made of a bioabsorbable material.

3. A staple cartridge as recited in claim 1 and further comprising a plurality of staples having ductile tissue penetrating legs, said staples being carried by said first cartridge body.

4. A staple cartridge as recited in claim 3 wherein said staples are arranged in plural rows.

5. A staple cartridge as recited in claim 1 wherein each cartridge body carries a plurality of staples having ductile tissue penetrating legs and said means for receiving said tissue penetrating legs of said staples is formed on both cartridge bodies.

6. A staple cartridge as recited in claim 1 wherein said cartridge bodies and said hinge are formed as an integral one-piece unit.

7. A staple cartridge as recited in claim 6 wherein transverse relief cuts are formed between staples to permit said cartridge bodies to bend.

8. A staple cartridge as recited in claim 1 wherein said receiving means includes a plurality of staple-forming anvils formed in opposed relation to said tissue penetrating legs.

9. A staple cartridge as recited in claim 8 wherein said staples are held in pockets formed in at least one of said cartridge bodies and further comprising means for driving said staples from said pockets.

10. A staple cartridge as recited in claim 1 wherein said receiving means includes a plurality of apertures formed in opposed relation to said tissue penetrating legs.

11. A staple cartridge as recited in claim 10 wherein said tissue penetrating legs of said staples are inserted through openings formed in said first cartridge body.

12. A staple cartridge as recited in claim 11 wherein said staples are arranged in plural rows.

13. A staple cartridge as recited in claim 12 wherein a line of weakening is defined in each cartridge body between a pair of said plural rows of staples.

14. A staple cartridge as recited in claim 10 wherein each cartridge body carries staples having ductile tissue penetrating legs in opposition to apertures formed in the other cartridge body.

15. A staple cartridge as recited in claim 10 wherein said apertures include camming surfaces against which said tissue penetrating legs are bent as they pass through said apertures.

16. A surgical stapler comprising
a housing;
an elongate tubular body with a proximal end mounted by said housing and a distal end including a pair of opposed jaws;
a plurality of staple cartridges disposed within said elongate tubular body, said staple cartridges each carrying at least one staple having a plurality of tissue penetrating legs;
said opposed jaws having a staple cartridge receiving position defining a space between said opposed jaws for receiving a staple cartridge; and
an advancing mechanism carried by said housing and including a member movable distally to advance a distalmost staple cartridge into said space between said opposed jaws.

17. A surgical stapler as recited in claim 16 and further comprising a tubular member removably disposed within said elongate tubular body, said plurality of staple cartridges being disposed within said tubular member and said tubular member including a stop at a distal end for limiting distal movement of said cartridges.

18. A surgical stapler as recited in claim 17 wherein said advancing mechanism includes bias means for biasing said staple cartridges distally such that said distalmost staple cartridge abuts said stop and means coupled with said distalmost staple cartridge for urging said distalmost staple cartridge past said stop.

19. A surgical stapler as recited in claim 18 wherein said urging means is a plunger extending proximally from said tubular member.

20. A surgical stapler as recited in claim 17 and further comprising a hub adapted to couple with said housing, wherein said tubular member is carried by said hub.

21. A surgical stapler as recited in claim 20 and further comprising a cap for closing a proximal end of said tubular member, said cap being removable to permit loading of staple cartridges into said tubular member.

22. A surgical stapler as recited in claim 16 and further comprising means coupled with said tubular body for at least partly closing said jaws to drive tissue penetrating legs of a staple disposed between said jaws in a cartridge through anatomical tissue held between said jaws.

23. A surgical stapler as recited in claim 22 wherein said means for closing said jaws includes an outer tubular member, said elongate tubular body being telescopically fitted within said outer tubular member and at least one of said outer tubular member and tubular body being movable relative to the other to close said jaws.

24. A surgical stapler as recited in claim 16 wherein said tubular body and jaws are formed as an integral one-piece unit.

25. A surgical stapler comprising a housing;

an outer tubular member having a proximal end mounted by said housing and terminating distally at a distal end;

an intermediate member having a tubular body disposed telescopically within said outer tubular member, a proximal end mounted by said housing and a distal end including a pair of opposed jaws resiliently biased apart;

a staple cartridge disposed within said opposed jaws, said staple cartridge carrying at least one staple having a plurality of tissue penetrating legs; and a handle coupled with at least one of said intermediate and outer tubular members to create relative movement between said intermediate and outer tubular members, whereby said pair of opposed jaws is closed around said staple cartridge when said distal end of said outer tubular member is advanced over said jaws and said tissue penetrating legs are driven through anatomical tissue held between said jaws.

26. A surgical stapler comprising a housing;

an outer tubular member having a proximal end mounted by said housing and terminating distally at a distal end;

an intermediate member having a tubular body disposed telescopically within said outer tubular member, a proximal end mounted by said housing and a distal end including a pair of opposed jaws resiliently biased apart;

an inner tubular member removably disposed at least partly within said intermediate member and carrying a plurality of staple cartridges;

an advancing mechanism including a member movable to advance at least one of said staple cartridges between said opposed jaws of said intermediate member; and a handle coupled with at least one of said intermediate and outer tubular members to create relative movement between said intermediate and outer tubular members, whereby said pair of opposed jaws is closed around said at least one staple cartridge when said distal end of said outer tubular member is advanced distally over said jaws.

27. A surgical stapler as recited in claim 26 wherein said inner tubular member includes a stop at a distal at a distal end for limiting distal movement of said cartridges.

28. A surgical stapler as recited in claim 26 wherein said advancing mechanism includes bias means for biasing said staple cartridges distally against said stop and means for urging said staple cartridges past said stop.

29. A surgical stapler as recited in claim 28 wherein said urging means includes a rod extending proximally from said inner tubular member.

30. A surgical stapler as recited in claim 26 and further comprising a hub adapted to couple with said housing, wherein said inner tubular member is carried by said hub.

31. A surgical stapler as recited in claim 30 and further comprising a cap for closing a proximal end of said inner tubular member, said cap being removable to permit loading of staple cartridges into said inner tubular member.

32. A method of stapling anatomical tissue comprising the steps of positioning the anatomical tissue between generally opposed, hingedly connected cartridge bodies of a staple cartridge;

compressing the staple cartridge around the anatomical tissue;

penetrating through the anatomical tissue with ductile tissue penetrating legs carried by a first of the cartridge bodies;

receiving the tissue penetrating legs in spaces defined by a second of the cartridge bodies; and bending the tissue penetrating legs to constrict the anatomical tissue.

33. A method of stapling anatomical tissue as recited in claim 32 wherein said cartridge bodies are formed of a bioabsorbable material and further comprising the step of, after bending the legs, leaving the cartridge bodies within the anatomical body.

34. A method of stapling anatomical tissue as recited in claim 33 wherein the step of receiving the tissue penetrating legs includes passing ends of the tissue penetrating legs through openings in the second cartridge body until they protrude, and the step of bending the tissue penetrating legs includes shaping the protruding ends of the tissue penetrating legs to bear against an outer surface of the second cartridge body.

35. A method of stapling anatomical tissue as recited in claim 32 and further comprising the steps of holding the staple cartridge between jaws of a surgical stapler when bending the tissue penetrating legs, opening the jaws after bending the tissue penetrating legs to create an open space between the jaws and advancing another staple cartridge between the jaws of the surgical stapler.

36. A method of stapling anatomical tissue as recited in claim 32 wherein the step of bending the tissue penetrating legs includes shaping the tissue penetrating legs against anvils formed in the second cartridge body.

37. A surgical staple cartridge comprising a pair of generally coextensive cartridge bodies adapted to fit within opposed jaws of a surgical stapler;

a staple having ductile tissue penetrating legs, said staple being carried by a first of said cartridge bodies; and a plurality of apertures formed in a second of said cartridge bodies in opposed relation to said tissue penetrating legs of said staple, said apertures receiving said tissue penetrating legs of said staple when said staple is driven through anatomical tissue positioned between said cartridge bodies.

38. A staple cartridge as recited in claim 37 wherein said cartridge bodies are made of a bioabsorbable material.

39. A staple cartridge as recited in claim 37 and further comprising a plurality of staples having ductile tissue penetrating legs, said staples being carried by said first cartridge body.

40. A staple cartridge as recited in claim 39 wherein said staples are arranged in plural rows.

41. A staple cartridge as recited in claim 40 wherein a line of weakening is defined in each cartridge body between a pair of said plural rows of staples.

42. A staple cartridge as recited in claim 39 wherein transverse relief cuts are formed between staples to permit said cartridge bodies to bend.

43. A staple cartridge as recited in claim 39 wherein said tissue penetrating legs of said staples are inserted through openings formed in said first cartridge body.

44. A staple cartridge as recited in claim 37 wherein each cartridge body carries a plurality of staples having ductile tissue penetrating legs and a plurality of apertures are formed in both cartridge bodies in opposed relation to said tissue penetrating legs.

45. A staple cartridge as recited in claim 37 wherein said apertures include camming surfaces against which said tissue penetrating legs are bent as they pass through said apertures.

46. A method of stapling anatomical tissue comprising the steps of positioning the anatomical tissue between generally opposed cartridge bodies of a staple cartridge;

compressing the staple cartridge around the anatomical tissue;

penetrating through the anatomical tissue with ductile tissue penetrating legs carried by a first of the cartridge bodies;

passing ends of the tissue penetrating legs through openings in the second cartridge body until the tissue penetrating legs protrude from the openings; and bending the protruding ends of the tissue penetrating legs against an outer surface of the second cartridge body to constrict the anatomical tissue.

47. A method of stapling anatomical tissue as recited in claim 46 wherein said cartridge bodies are formed of a bioabsorbable material and further comprising the step of, after bending the legs, leaving the cartridge bodies within the anatomical body.

48. A method of stapling anatomical tissue as recited in claim 46 and further comprising the steps of holding the staple cartridge between jaws of a surgical stapler when bending the tissue penetrating legs, opening the jaws after bending the tissue penetrating legs to create an open space between the jaws and advancing another staple cartridge between the jaws of the surgical stapler.

* * * * *